(12) United States Patent
Salerno

(10) Patent No.: US 12,740,795 B2
(45) Date of Patent: Sep. 22, 2026

(54) INTRALUMINAL VASCULAR DEVICE, PARTICULARLY FOR SCLEROTHERAPY, AND METHOD

(71) Applicant: I-VASC S.R.L., Milan (IT)

(72) Inventor: Mario Salerno, Milan (IT)

(73) Assignee: I-VASC S.R.L., Milan (IT)

( * ) Notice: Subject to any disclaimer, the term of this patent is extended or adjusted under 35 U.S.C. 154(b) by 714 days.

(21) Appl. No.: 18/250,831

(22) PCT Filed: Oct. 28, 2021

(86) PCT No.: PCT/IB2021/059974

§ 371 (c)(1),
(2) Date: Apr. 27, 2023

(87) PCT Pub. No.: WO2022/090989

PCT Pub. Date: May 5, 2022

(65) Prior Publication Data

US 2023/0404606 A1 Dec. 21, 2023

(30) Foreign Application Priority Data

Oct. 30, 2020 (IT) ........................ 102020000025918

(51) Int. Cl.

| | |
|---|---|
| ***A61B 17/22*** | (2006.01) |
| ***A61B 17/00*** | (2006.01) |
| ***A61B 17/32*** | (2006.01) |
| ***A61B 17/3207*** | (2006.01) |
| ***A61M 25/10*** | (2013.01) |

(52) U.S. Cl.

CPC .................. *A61B 17/22032* (2013.01); *A61B 17/320725* (2013.01); *A61B 2017/00557* (2013.01);

(Continued)

(58) Field of Classification Search

CPC ...... A61B 17/22032; A61B 17/320725; A61B 2017/00557; A61B 2017/320004;

(Continued)

(56) References Cited

U.S. PATENT DOCUMENTS

| | | | | |
|---|---|---|---|---|
| 5,112,347 A * | 5/1992 | Taheri | A61B 17/22032 | 604/541 |
| 6,394,978 B1 * | 5/2002 | Boyle | A61M 25/1002 | 604/104 |

(Continued)

FOREIGN PATENT DOCUMENTS

| | | |
|---|---|---|
| DE | 2847633 A1 | 5/1979 |
| EP | 0937482 A2 | 8/1999 |
| EP | 2120738 B1 | 3/2016 |

OTHER PUBLICATIONS

International Search Report for International Patent Application No. PCT/IB2021/059974, Jan. 25, 2022.

(Continued)

*Primary Examiner* — Bradley J Osinski
(74) *Attorney, Agent, or Firm* — Armstrong Teasdale LLP

(57) ABSTRACT

A vascular device for treating a tract of a blood vessel has an intraluminal element having at least one dispensing opening for dispensing a pharmacological agent in the tract of the blood vessel, and an abrasion element coming into contact with an inner wall of the blood vessel to remove material from the inner wall. The abrasion element has a contact portion for removing the material and a collection portion for collecting the removed material. and is configured to expand between a rest configuration and a contact configuration. The abrasion element has a first surface facing the intraluminal element and configured to face a fluid inside the blood vessel. The first surface in the contact configuration forms a concave portion adapted to face the fluid inside the blood vessel. The collection portion includes the concave (Continued)

Figure 5:
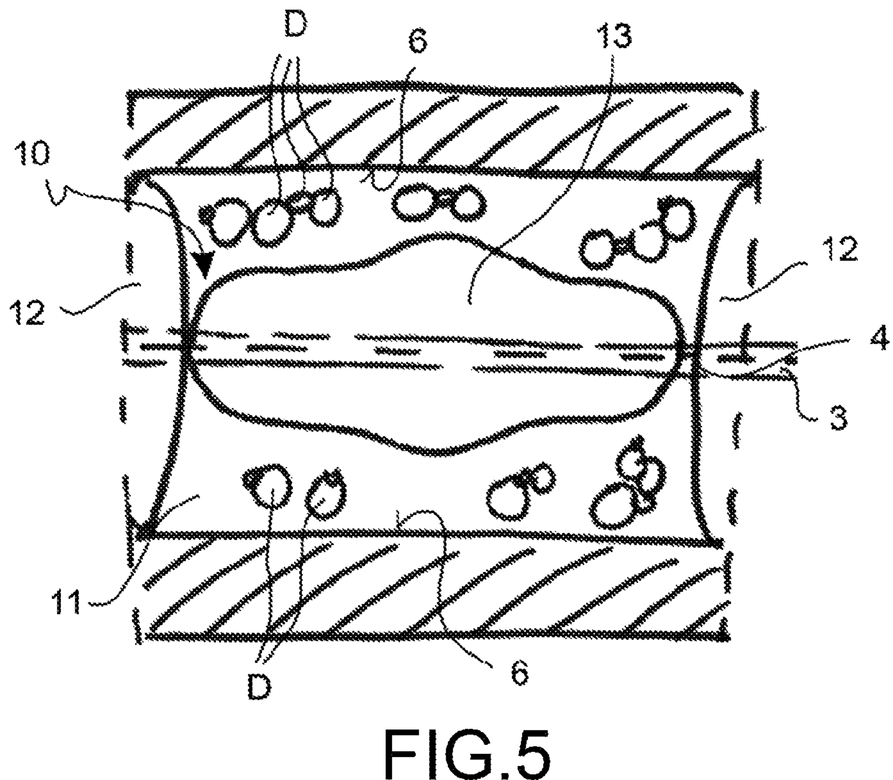

portion to collect the material removed from the inner wall treated with the pharmacological agent.

20 Claims, 14 Drawing Sheets

(52) U.S. Cl.
CPC ............... *A61B 2017/22082* (2013.01); *A61B 2017/320004* (2013.01); *A61B 2017/320064* (2013.01); *A61M 25/1002* (2013.01); *A61M 2025/109* (2013.01)

(58) Field of Classification Search
CPC .. A61B 2017/320064; A61M 25/1002; A61M 2025/109
See application file for complete search history.

(56) References Cited

U.S. PATENT DOCUMENTS 7,914,549 B2 * 3/2011 Morsi ............ A61B 17/320725 606/200
2005/0055040 A1 3/2005 Tal
2012/0059356 A1 3/2012 di Palma et al.
2013/0030410 A1 * 1/2013 Drasler .................. A61B 18/04 604/510
2013/0110081 A1 5/2013 Roorda et al.
2014/0276608 A1 9/2014 Roorda et al.
2016/0030023 A1 2/2016 Hayakawa et al.
2016/0302822 A1 10/2016 Tal et al.
2019/0125322 A1 5/2019 Brandeis
2020/0113575 A1 4/2020 Wisnosky et al.

OTHER PUBLICATIONS

Whiteley M.S. et al., Media Damage Following Detergent Sclerotherapy Appears to be Secondary to the Induction of Inflammation and Apoptosis: An Immunohistochemical Study Elucidating Previous Histological Observations, European Journal of Vascular and Endovascular Surgery, Mar. 2016, pp. 421-428, vol. 51, Issue 3, Elsevier Ltd.

* cited by examiner

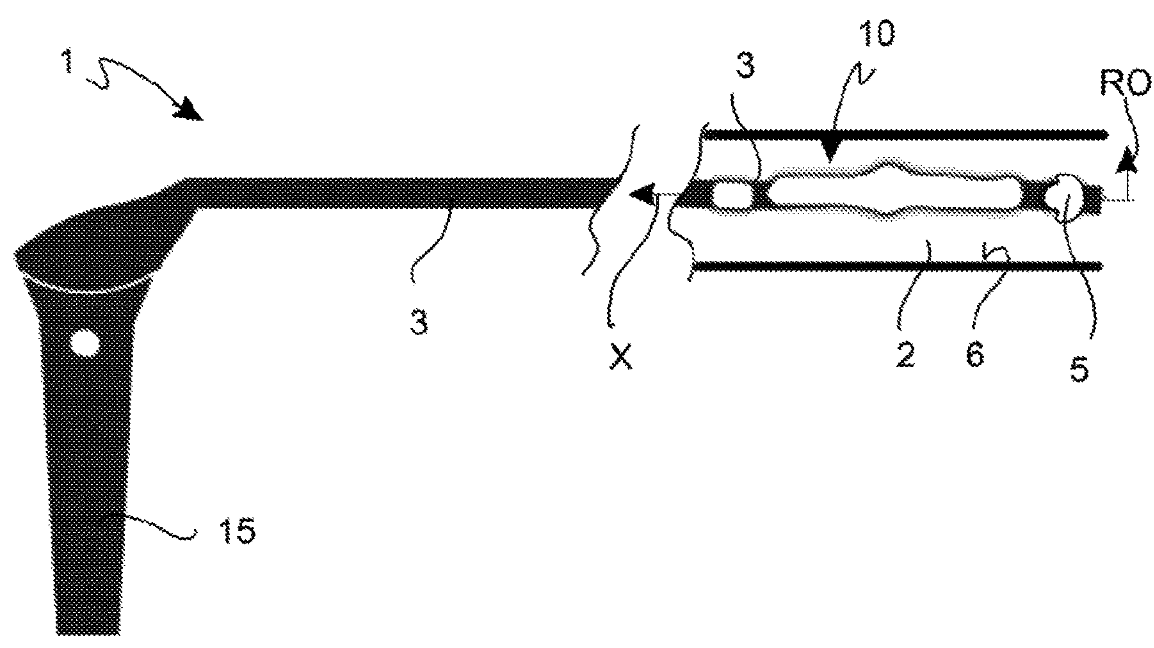
FIG.1
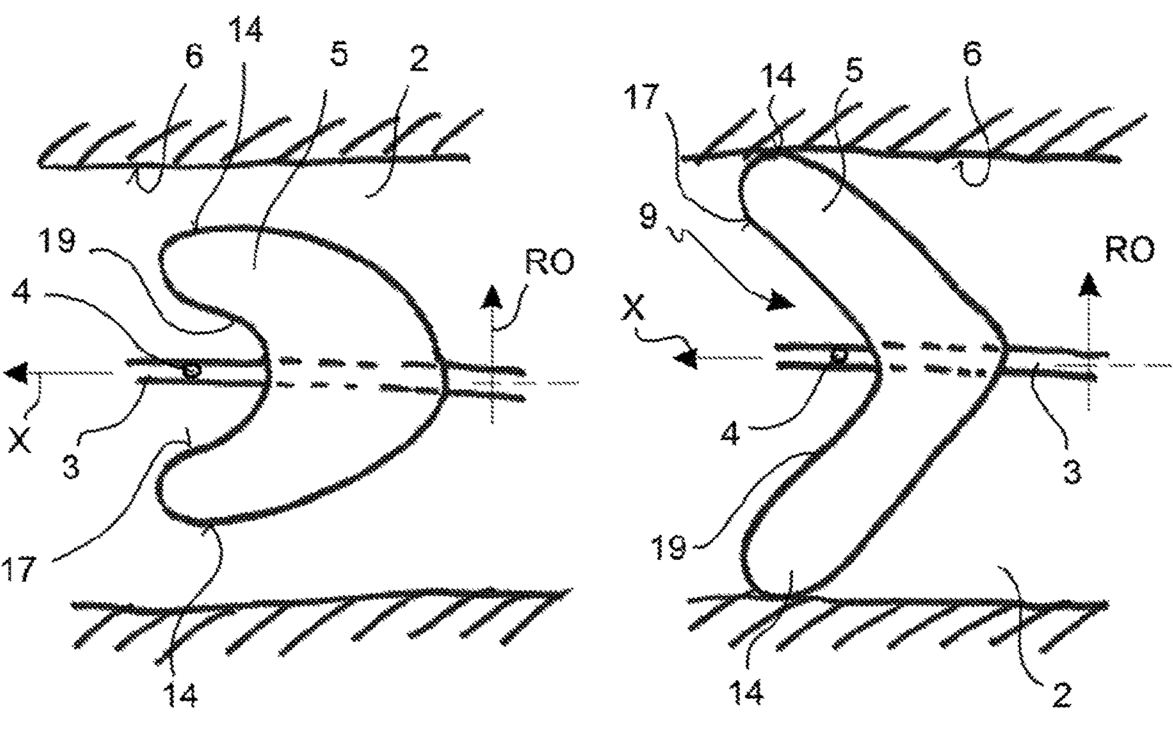
FIG.2 A
FIG.2 B

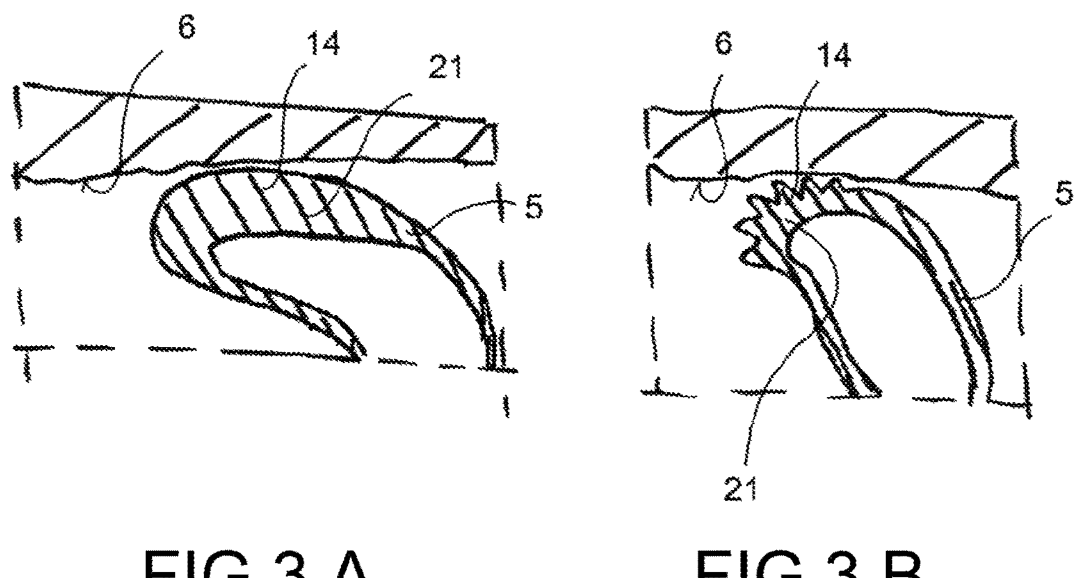
FIG.3 A
FIG.3 B
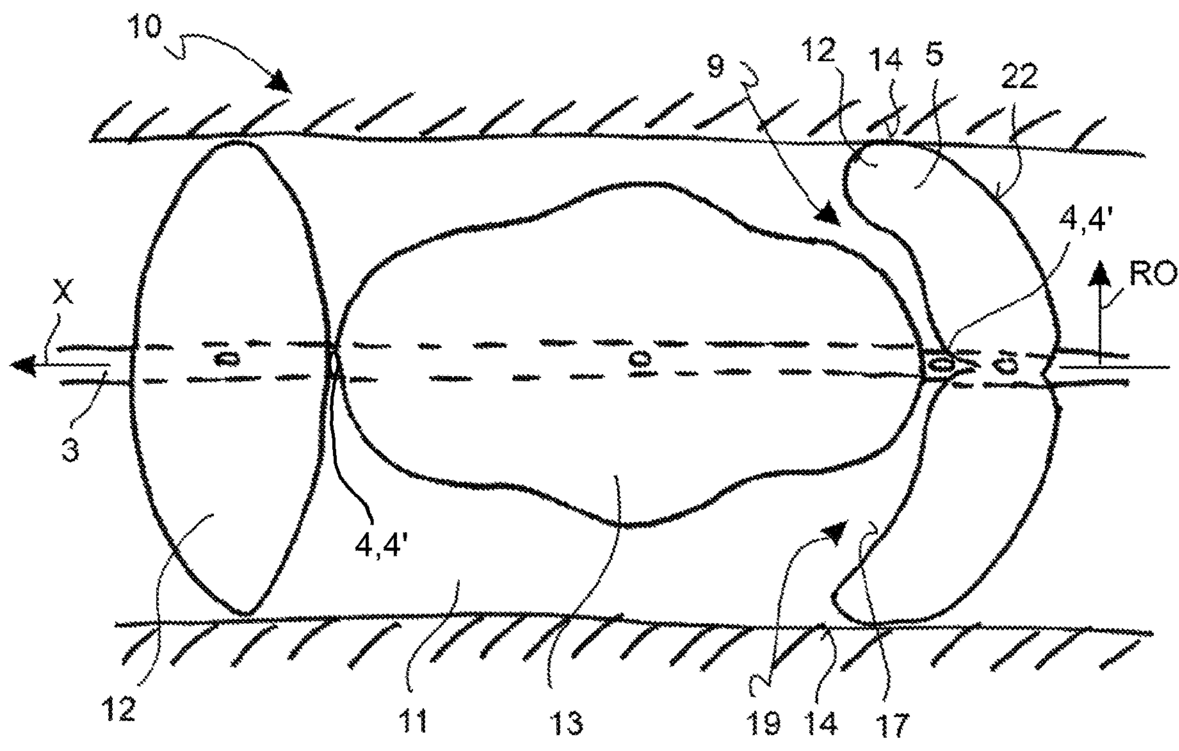
FIG.4

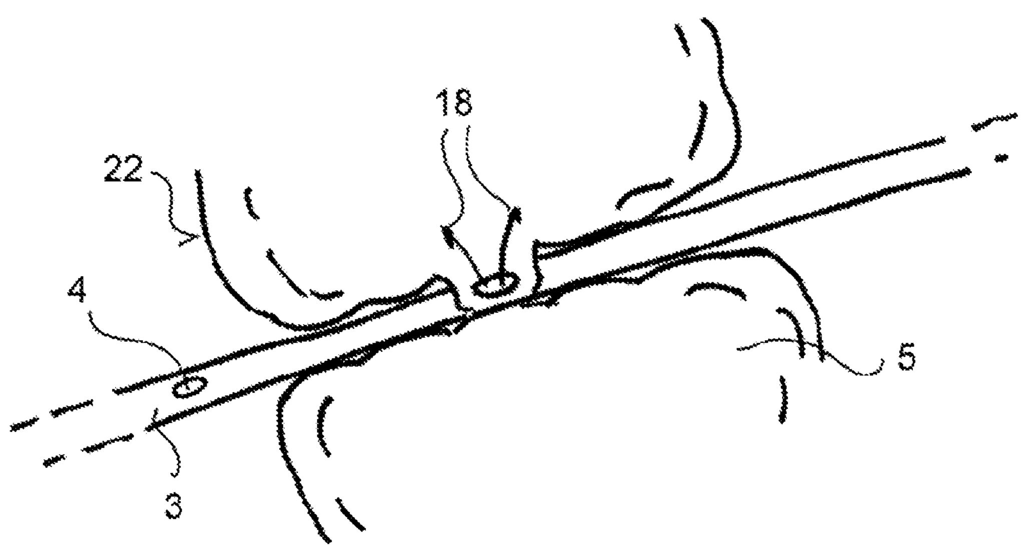
FIG.7
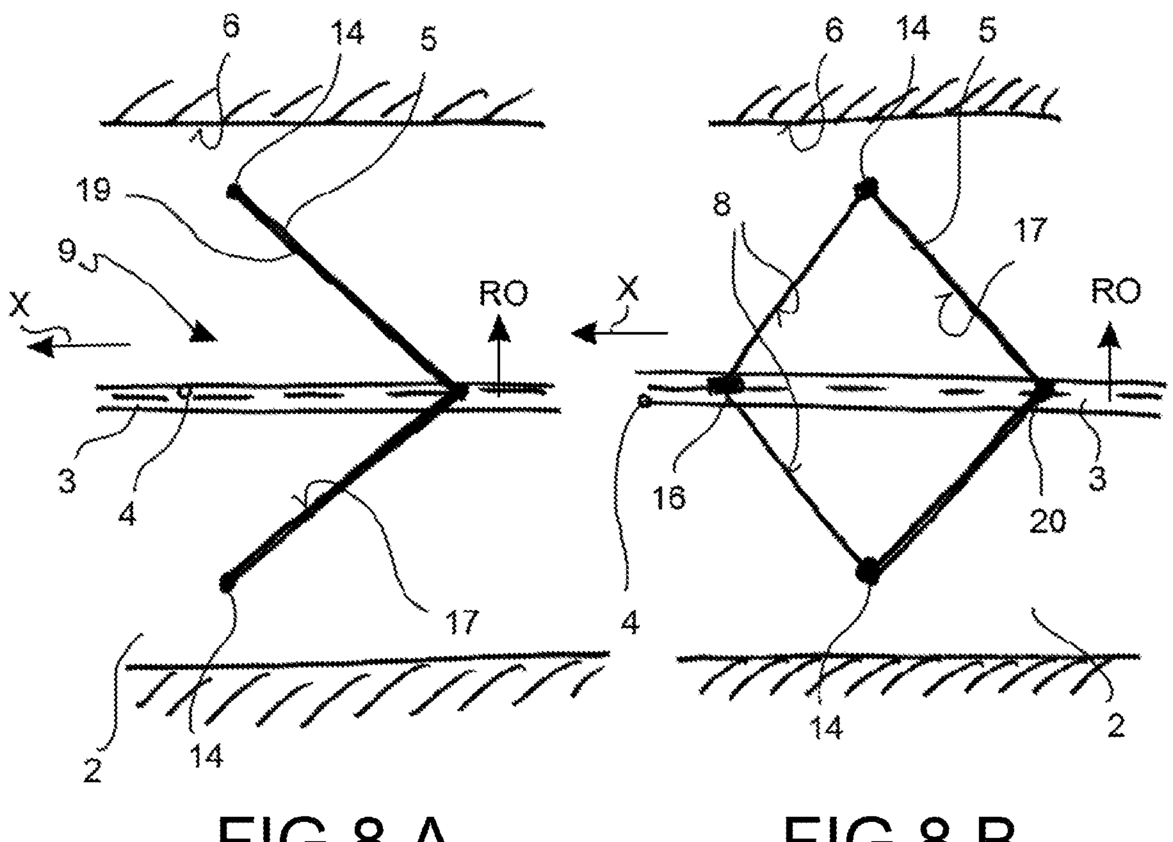
FIG.8 A
FIG.8 B

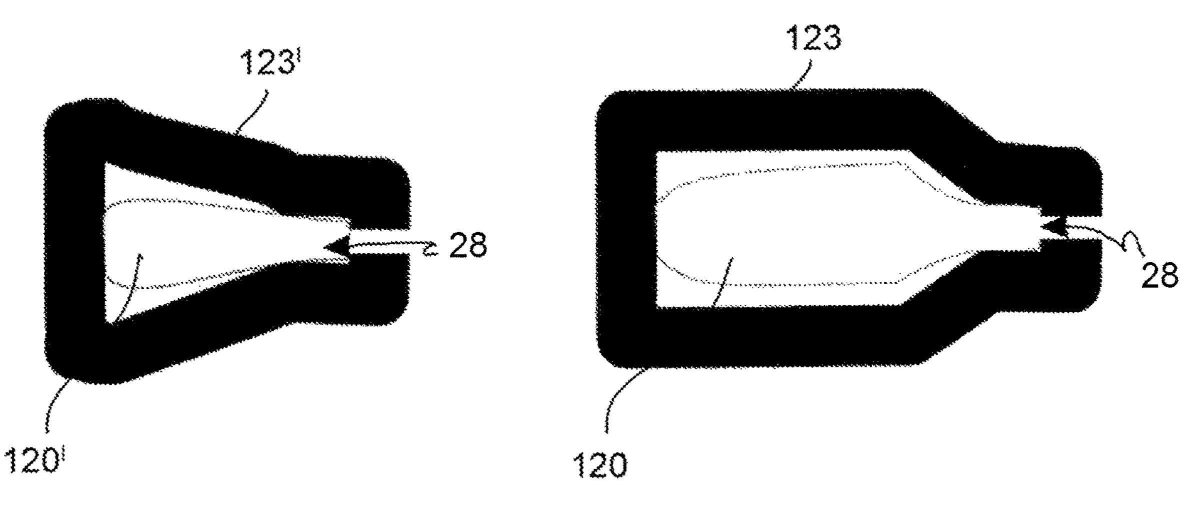
FIG. 17 A
FIG. 17 B
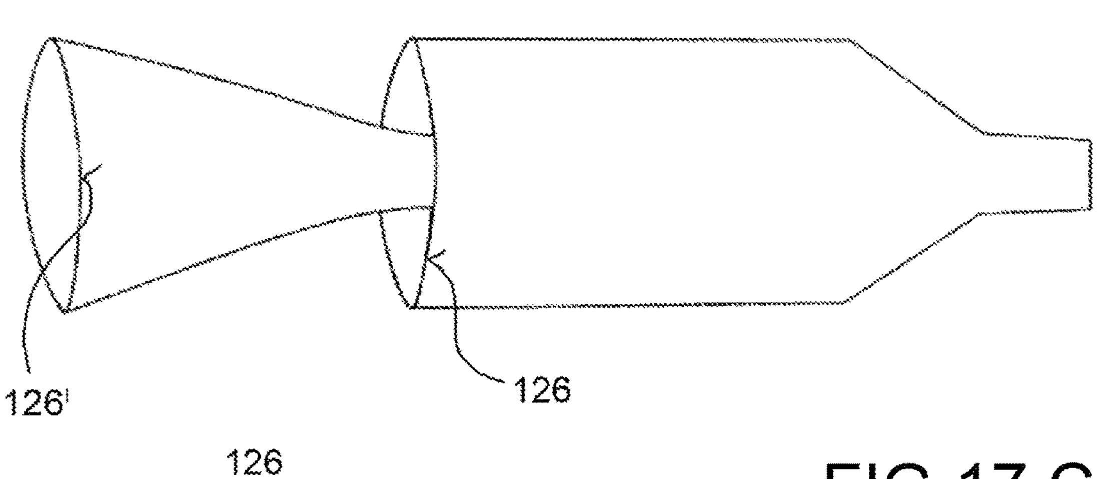
FIG.17 C
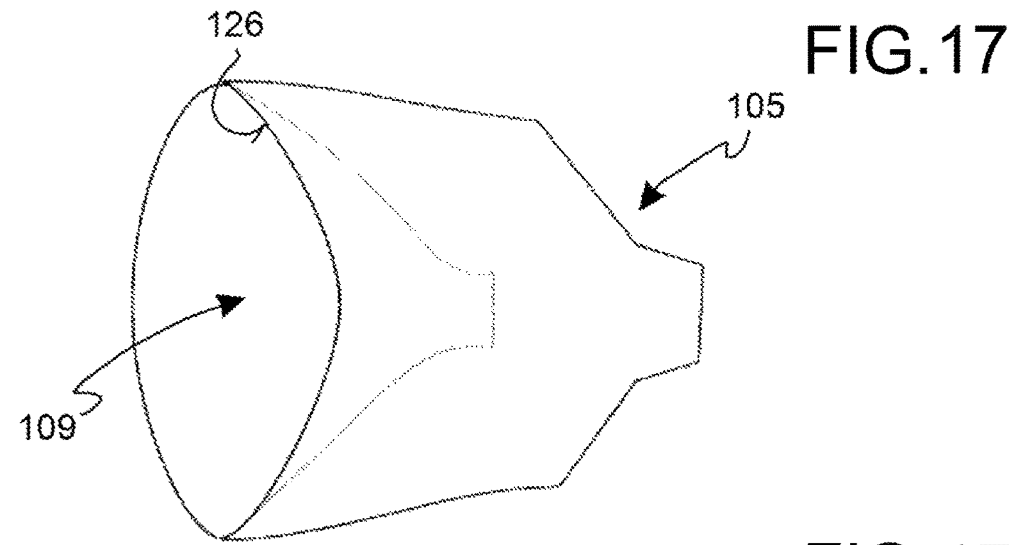
FIG.17 D

INTRALUMINAL VASCULAR DEVICE, PARTICULARLY FOR SCLEROTHERAPY, AND METHOD

CROSS-REFERENCE TO RELATED APPLICATIONS

This application is a National Stage Application of International Patent Application No. PCT/IB2021/059974, having an International Filing Date of Oct. 28, 2021, which claims priority to Italian Application No. 102020000025918 filed Oct. 30, 2020, the entire contents of each of which are hereby incorporated by reference herein.

FIELD OF THE INVENTION

The subject of the present invention is a vascular device for treating a blood vessel.

A device according to the present invention is applicable in the context of a sclerosing treatment.

The present invention further relates to a method for treating a blood vessel.

PRIOR ART

The sclerosing treatment of varices typically includes the use of pharmacological agents with the aim of bringing an effective quantity of drug in contact with the inner wall of the blood vessel to be treated.

Patent EP-2120738-B1 of the same Applicant discloses an embodiment of a catheter provided with expandable balloons which expand to isolate from the blood circulation an annular chamber inside the blood vessel in which to inject the sclerosing drug in a controlled manner. The presence of such radially expandable balloons, which isolate an annular chamber between the catheter shaft and the vessel wall, avoids having to inject the drug in the entire section of the vessel stretch to be treated, allowing the drug to be injected only in one annular area of the blood vessel in contact with the wall. The device disclosed therein allows performing empty vein sclerotherapy, without blood, therefore without plasma proteins which can neutralize the pharmacological activity of the sclerosing drug; this allows a fine control of the concentration of the drug injected on the inner wall of the vein; it allows positioning the drug comprehensively on the entire inner vein surface and it also allows managing a time of drug contact with the vein wall. The drug-to-part contact time is critical to allow the drug to penetrate the inner wall thickness of the vein and generate an inflammatory vein repair response.

Document US-2013-110081 shows a catheter solution for occlusion of a blood vessel section comprising expandable bellows occlusion elements slidably fitted on the catheter shaft and adapted to radially expand when subjected to a predefined longitudinal compression movement directed along the catheter shaft.

Document US-2014-276608 discloses an expandable balloon having a double layer wall forming a gap, the outer layer of the double wall of the balloon being porous to allow the drug to be sprinkled into the gap directly on the wall.

The solutions mentioned above disclose an essentially pharmacological approach. The treatment of the inner wall of the vessel is performed by the drug, sprinkled by means of the vascular catheter, which reaches the endothelium of the inner wall of the vessel, within a certain time of contact of the drug with the wall, at a certain concentration of the drug near the inner wall of the vessel.

It has also been proposed to use a vascular catheter having a rotating rod to direct the drug towards the blood vessel wall, as shown for example by document US-2016-302822. The free end of the rotating rod is also capable of damaging the inner wall of the vessel, creating lesions. According to such a disclosure, first mechanical damage is carried out on the healthy wall and then chemical damage on the previously mechanically damaged part. The mechanical damage has the purpose of creating micro-fissures on the vascular wall useful to let the drug enter the thickness of the wall so as to be able to perform a deep treatment, or of the muscular layer which is the layer below the endothelium (typically the layer of endothelium has a thickness of the order of 5 micrometers). Therefore, according to these teachings, it is the pharmacological treatment of the muscular layer (the layer below the endothelium) which determines the success of the treatment, as also supported in the study published in the reference: M. S. Whiteley et al., "Media damage following detergent sclerotherapy appears to be secondary to the induction of inflammation and apoptosis: an immunohistochemical study elucidating previous histological observations", Eur. J. Vasc: Endovasc. Surg. (2016) 51, 421-428.

Document US-2005-055040 discloses a vascular catheter solution capable of dispensing sclerosing drug after an ablation operation of material from the blood vessel wall performed by the rotating head of the distal end of the catheter shaft, so that by the effect of the lesions created on the endothelium of the inner wall of the vessel, the sclerosing drug is favorably absorbed deeper in the wall. However, this solution is by no means without drawbacks or limitations: first of all it is not possible to know if the mechanical damage is homogeneous over the entire inner surface of the vein, and in particular in the case of large-caliber veins, where the angled tip of the catheter which is a few millimeters in length, by rotating, expresses a circumference with a radius of less than about 10 millimeters, therefore not able to homogeneously damage the inner wall of large-caliber veins. Furthermore, the debris scraped from the vessel wall is necessarily released into the bloodstream and being mainly dead tissue or substances of endothelial origin such as endothelin, a powerful vasoconstrictor, they are potentially toxic as they can easily cause the onset of procoagulative reactions at a distance. In fact, it has been shown that a mechanical, chemical or biochemical insult of the endothelium generates the release of endothelin with an increase in this molecule circulating in the bloodstream. Endothelin is capable of generating a powerful spasm, or closing the arterioles with consequent reduction of the blood supply and therefore of oxygen to the affected organ. Circulating in the bloodstream, the endothelin reaches small vessels of various organs such as: heart, kidneys and brain and at such a level the vasospasm, or closure of the arterioles which carry blood to the parenchyma of such organs, can cause significant symptoms such as angina, heart attacks, cerebral or cerebellar ischemia, etc.

The need is therefore strongly felt to provide a solution of improved efficacy in the context of the sclerosing treatment of a blood vessel, be it of small, medium or large caliber.

The need is also felt to prevent any potential undesirable effects related to the release of dead circulating cells, catabolites, etc. in the bloodstream.

SUMMARY OF THE INVENTION

An object of the present invention is to obviate the drawbacks of the known art mentioned up to now and to provide a solution to the need to devise an improvement in the sclerosing treatment of a blood vessel.

This and other objects are achieved by a vascular device as described and claimed herein.

Some advantageous embodiments are the subject of the dependent claims.

It is clear that the appended claims are an integral part of the present description.

According to an aspect of the invention, a vascular device for treating a blood vessel, for example sclerotherapy, comprises an intraluminal element, for example a catheter shaft, provided with an abrasion element intended to come into contact with the inner wall of the blood vessel to remove material from the inner wall of the blood vessel, in which the abrasion element comprises a collection portion adapted to collect the removed material, avoiding dispersing the removed material as well as residues of pharmacological agent in the circulatory stream.

According to an aspect of the invention, the abrasion element is for example an expandable deformable element, meaning here by expandable even only that the deformable element is, when seen in profile, liftable with respect to the profile of the catheter shaft, adapted to selectively assume a contact configuration in which it is in contact with the inner wall and a rest configuration in which it is spaced from the inner wall. The contact configuration can be determined by the degree of expansion of the abrasion element. For example, the expandable element is an inflatable balloon and by adjusting the inflation of the balloon it is possible to make the inflatable balloon assume the contact configuration, thus acting as an abrasion element of the inner wall of the vessel.

According to an aspect of the invention, the abrasion element comprises at least one surface facing the intraluminal element and configured to face the fluid inside the blood vessel at least in the contact configuration, forming a concave portion adapted to collect the material removed from the inner wall and treated with a pharmacological agent.

Preferably, the vascular device further comprises a vessel treatment assembly adapted to isolate a volume of blood vessel in contact with the inner wall of the vessel in order to inject a certain amount of drug therein in a controlled manner.

According to a preferred operating mode, first a pharmacological treatment is performed, for example using a sclerosing drug, on a certain blood vessel section, and then a mechanical abrasion of the wall is performed in order to scrape the inner wall after the application of the pharmacological agent, thus removing material from the inner wall of the vessel. Preferably, a collection of the mechanically abraded material from the pharmacologically treated inner wall of the blood vessel is also included.

The aforementioned sequence, i.e., first the chemical treatment then the mechanical treatment and at the same time the collection of the abraded material also has another meaning or value in the fact that the removal of the endothelium and part of the muscular layer is necessary to start the reparative process of the vein wall to form a persistent scar which closes the vein. The scarring closure of the vein is the main goal of a sclerotherapy treatment of diseased veins such as varicose veins. A mechanical abrasion of the healthy inner part of the vein performed with balloon catheters, alone or performed before the sclerosing treatment, already described in the literature, did not give positive effects in terms of healing.

The pharmacological treatment is preferably performed by the vessel treatment assembly. The vessel treatment assembly comprises an intraluminal element outlet hole for drug dispensing. The vessel treatment assembly can comprise plug elements adapted to isolate a blood vessel tract from circulation, and a core element adapted to form, together with said plug elements, a blood vessel volume in contact with the blood vessel wall. For example the core element comprises a radially expandable inflatable balloon which is fitted on the intraluminal element, for example a shaft of a vascular catheter, forming a substantially annular chamber, or volume, in contact with the vessel wall and preferably the plug elements partially enclose said annular chamber, in which the outlet hole for dispensing the drug opens into said chamber.

The treatment assembly comprises a path in communication with the chamber or volume, for example placed along the intraluminal element, for example a catheter shaft, so as to supply the chamber or volume with the drug.

One of said plug elements can also act as an abrasion element of the pharmacologically treated portion of the wall which consists of dead cells.

A path can be included inside the intraluminal element, for example a catheter shaft, to manage the expansion degree of the abrasion element. When one of said plug elements also acts as an abrasion element of the pharmacologically treated portion of the wall, a path can be included inside the intraluminal element, for example a catheter shaft, which manages the expansion degree both of the plug and of the abrasion element.

Upon completion of the pharmacological treatment of a blood vessel tract, the chamber or volume delimited by the treatment assembly can be fed along the blood vessel to treat a new blood vessel tract. The abrasion element is preferably placed behind, with respect to the advance direction of the chamber delimited by the treatment assembly, so as to exert an abrasive action on the portion of the inner wall of the blood vessel just treated pharmacologically during the repositioning of the chamber of the treatment assembly. When one of said plug elements also acts as an abrasion element of the damaged inner wall portion, the abrasion can occur while the drug is in contact with the inner wall of the vessel.

The abrasion element can be shaped so as to expose a collection portion to the advance direction to collect the material removed from the inner wall of the vessel. The collection portion can be placed near the intraluminal element, for example a catheter shaft, and around it, and can be obtained by the shape of the abrasion element, for example a concave shape with respect to the advance direction, e.g., conical.

The advance direction can be directed proximally, i.e., towards the surgeon maneuvering the vascular catheter, and in this case the at least one abrasion element is placed distal to the drug dispensing opening, so that by proximally feeding the vascular catheter first a pharmacological treatment and after a mechanical abrasion treatment are obtained on the same circumferential transverse section of the blood vessel.

The abrasion element can be of such shape and material as to form a sail effect during the feeding, so that the abrasion element substantially acts as a sail with respect to the fluid current due to the feeding movement of the abrasion element in the blood vessel, which can be an element which also acts as a chamber plug. Thereby, the abrasion element can expand by the sail effect, obtaining the contact configuration precisely due to the feeding of the vascular device in the patient's blood vessel.

By virtue of the proposed solutions, it is possible to remove the endothelial layer of the inner wall of the blood vessel and part of the muscular layer consisting of dead, damaged or injured cells due to the application of the sclerosing pharmacological agent. Removing the dead cell layer of the inner part of the vein after the sclerosing action is essential to allow the underlying live cell state to be activated so as to generate a homogeneous fibrotic repair tissue which leads to complete and permanent occlusion of the sclerotic blood vessel. Such a process is faster if the body does not have to spend time removing the layer of dead cells due to the drug, and by virtue of the proposed solutions the step of removing the layer of dead cells is performed by the abrasion element of the vascular device. In nature, the dead tissue elimination process is carried out by macrophage cells which are activated by the release of chemical substances related to local inflammatory processes activated by necrotic tissue. The elimination of this dead cellular tissue by means of macrophages can also take quite a long time, thus slowing down the repair and scarring processes of the vein, slowing down healing. An excess inflammatory reaction related to the abundant tissue necrotized by the drug can then in turn generate potentially harmful and annoying local inflammatory reactions in the patient treated with sclerotherapy.

Another aspect to consider is that related to the release of cellular metabolites such as endothelin, which is released in the bloodstream after damage to the endothelial cells. Endothelin is a powerful vasoconstrictor and can generate vasospasm of various arterioles, for example cerebral, cardiac, etc., with neurological or cardiac side effects. The release of dead cells in the bloodstream determines thrombotic micro-aggregation phenomena with the formation of circulating micro-emboli which can reach the lungs and is therefore highly undesirable. By virtue of the proposed solutions, it is advantageously possible to collect the dead tissue removed from the inner wall of the blood vessel.

To obtain an abrasion element, it is possible to proceed by including an expandable balloon made as a through deformable body which delimits a longitudinal through cavity with the surface thereof facing the intraluminal element, fitting the through deformable body on the intraluminal element and fastening it tightly to the intraluminal element by means of a fastening element so that a free edge opposite the fastening element is formed, and subsequently overturning the free edge, and fastening the free edge to the intraluminal element by means of a fastening element, and forming a chamber which can be inflated by inflation fluid.

To make an abrasion element, it is possible to proceed by including an expandable balloon made by molding in a mold cavity having at least one concave portion.

FIGURES

Figure 6:
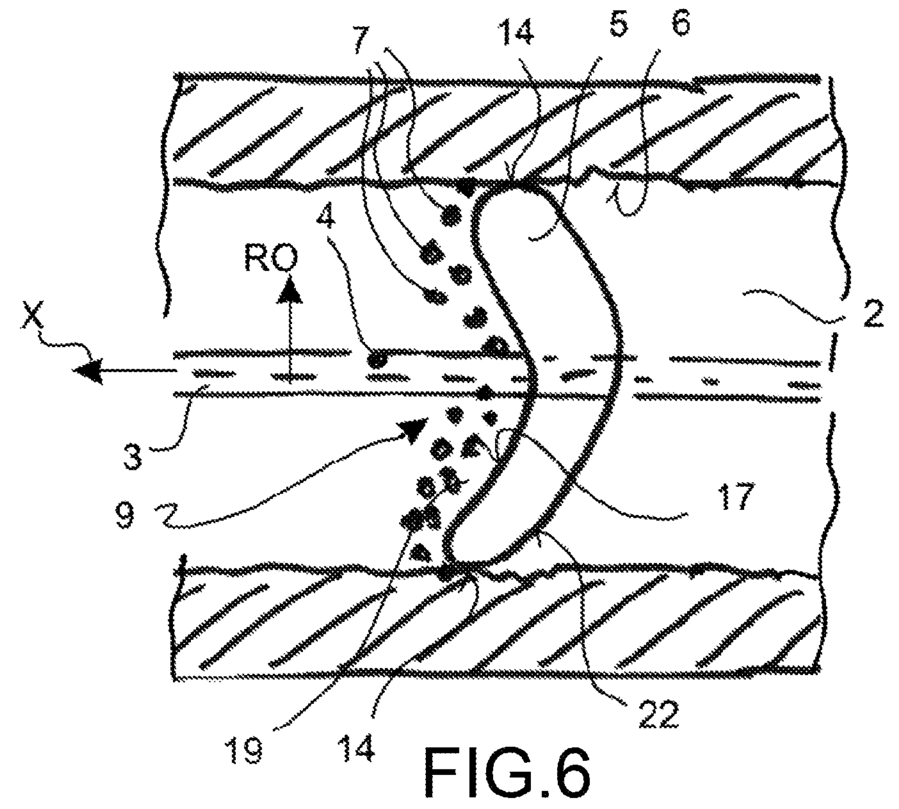
Figure 9:
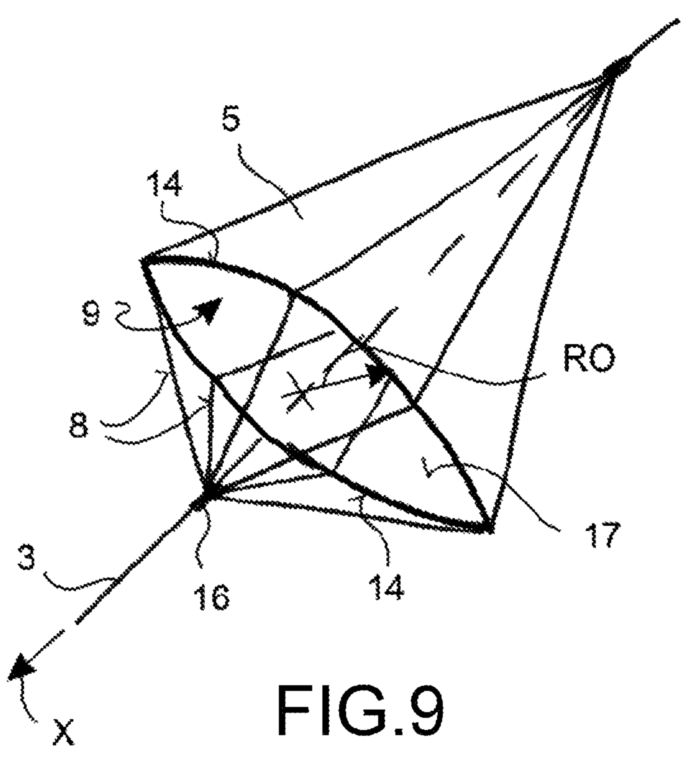
Figure 10:
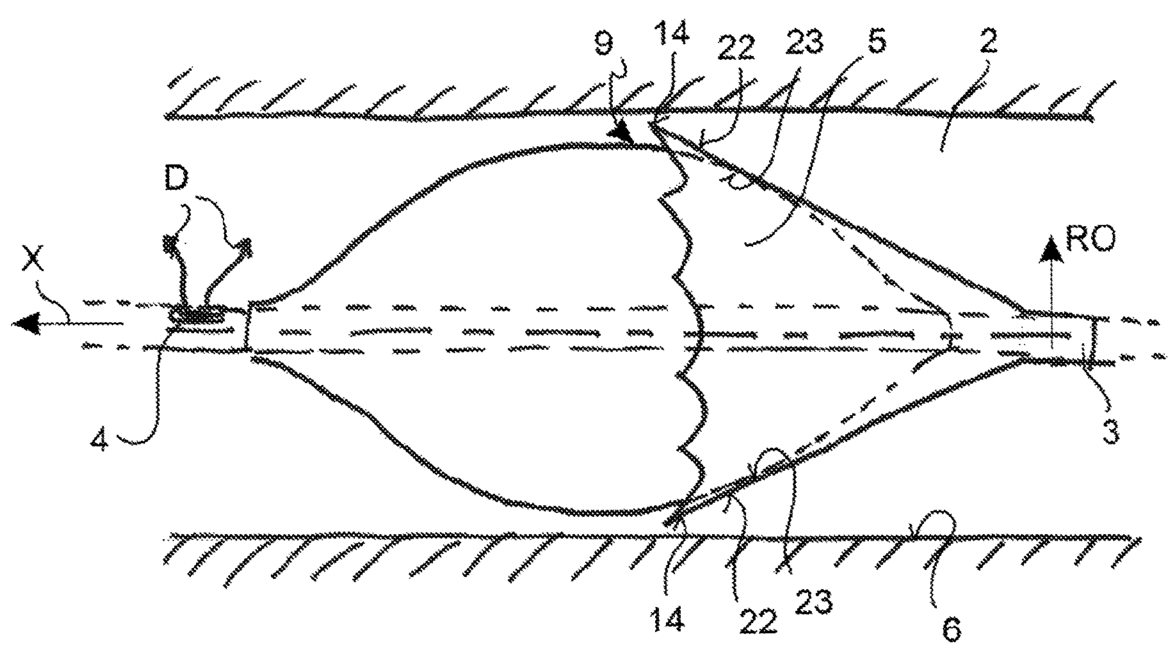
Figure 11:
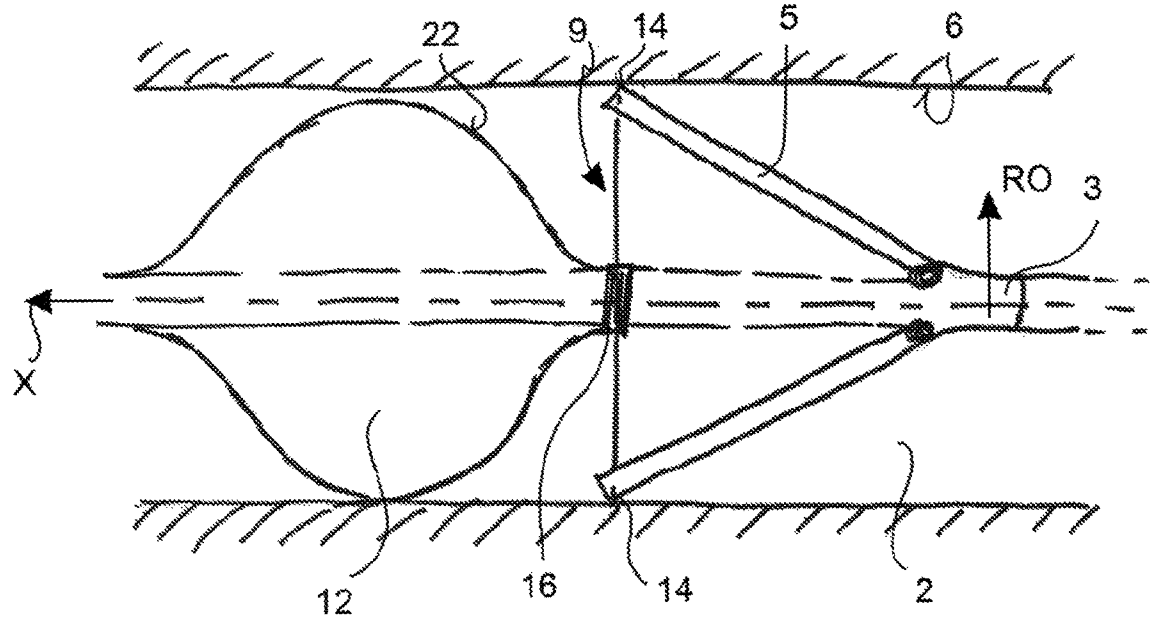
Figure 12:
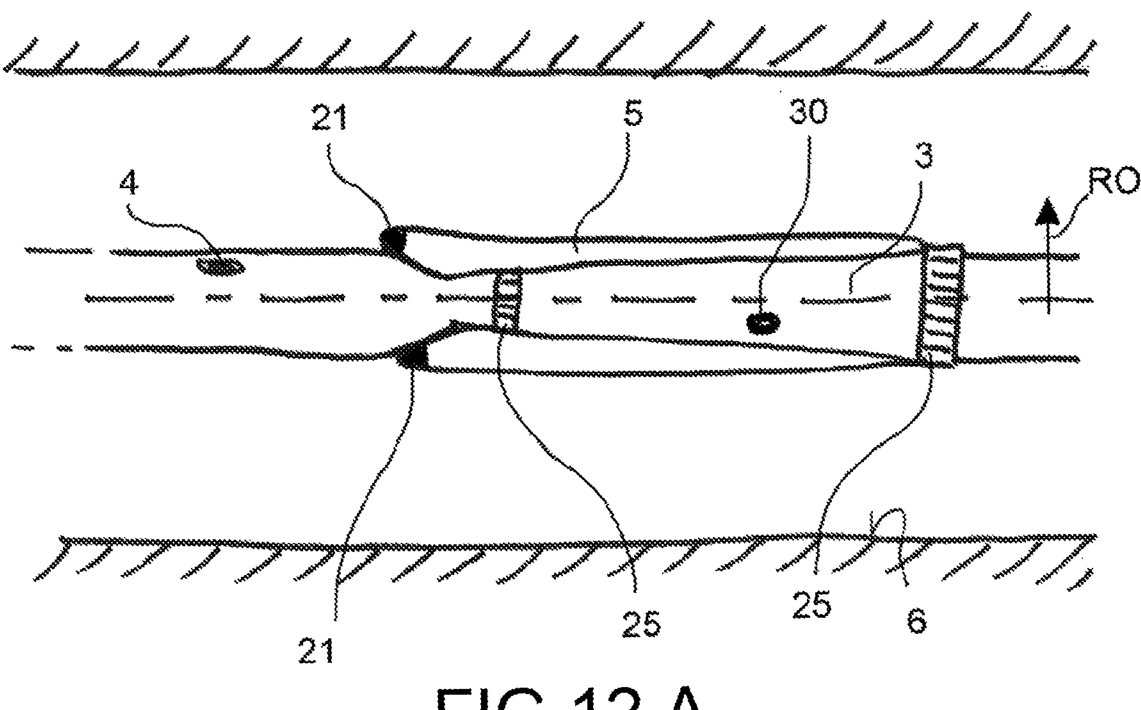
Figure 13:
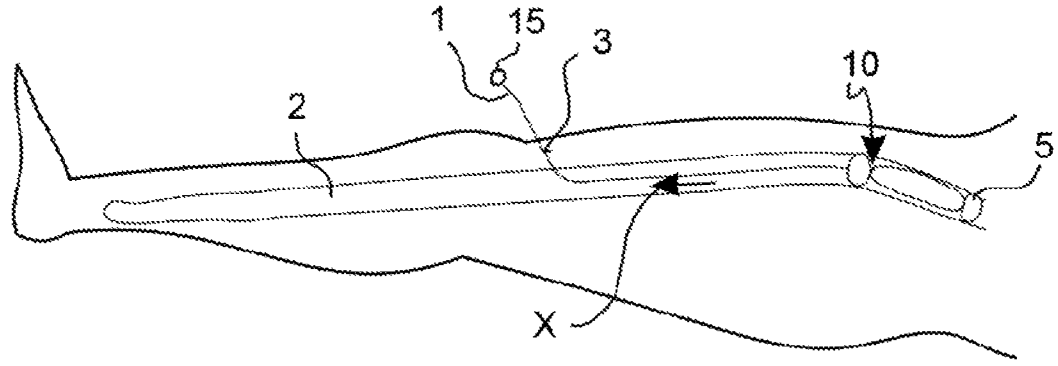
Figure 13:
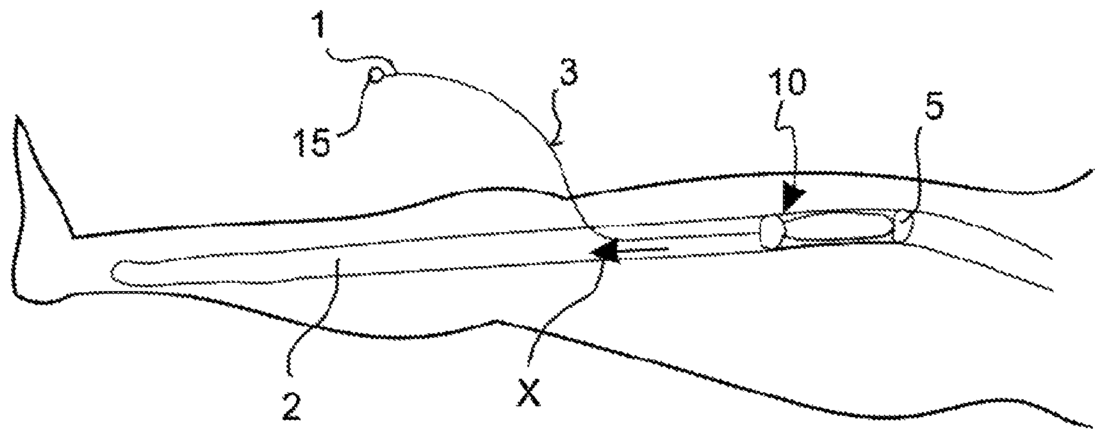
Figure 13:
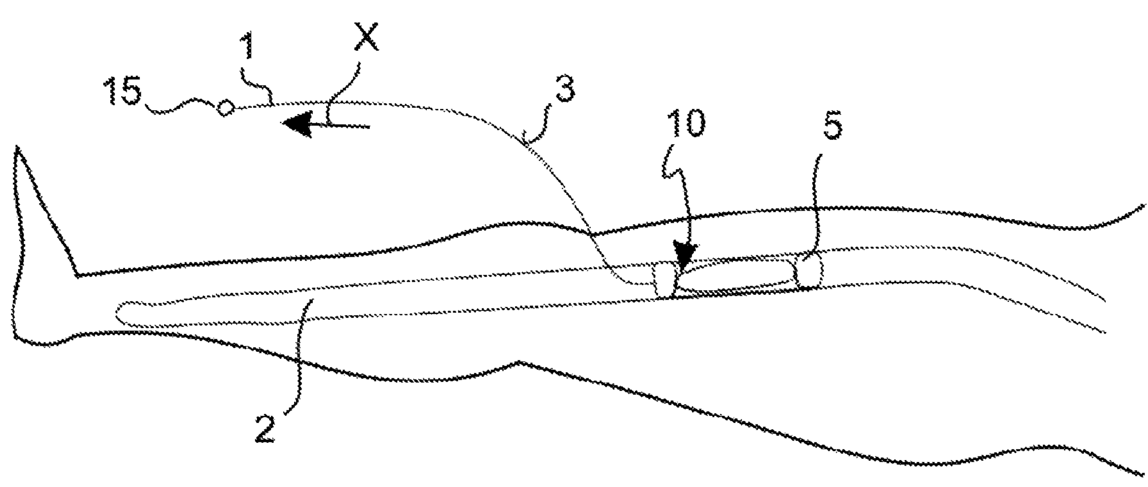
Figure 14:
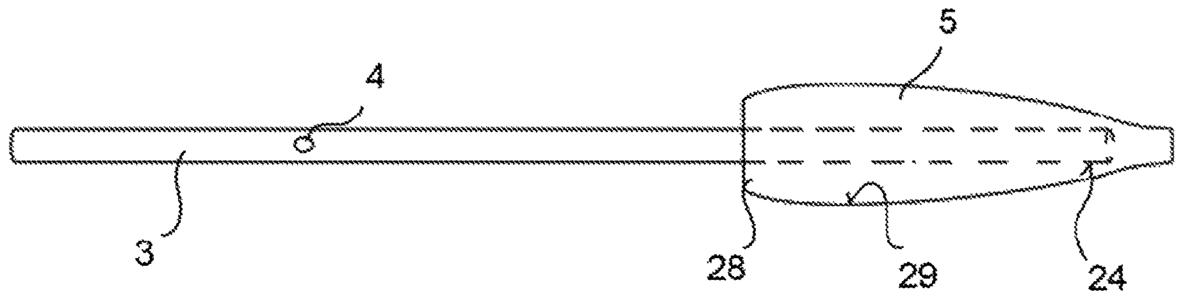
Figure 14:
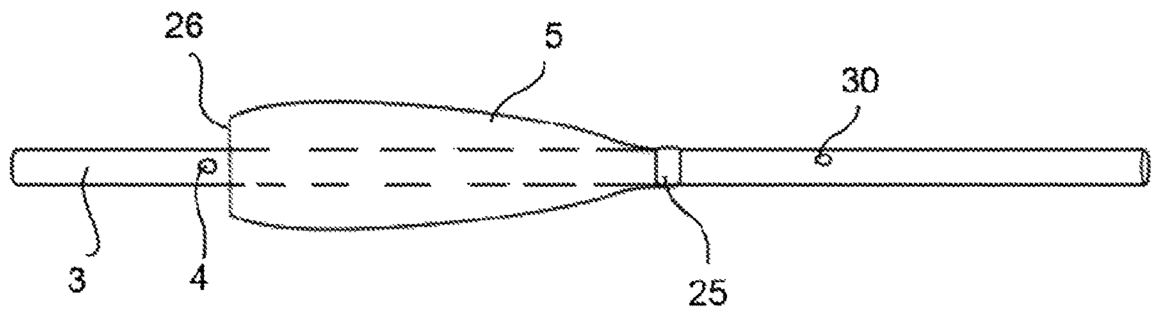
Figure 14:
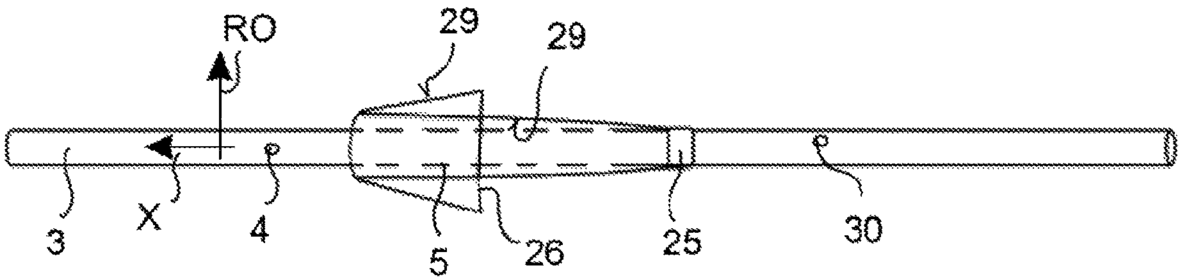
Figure 14:
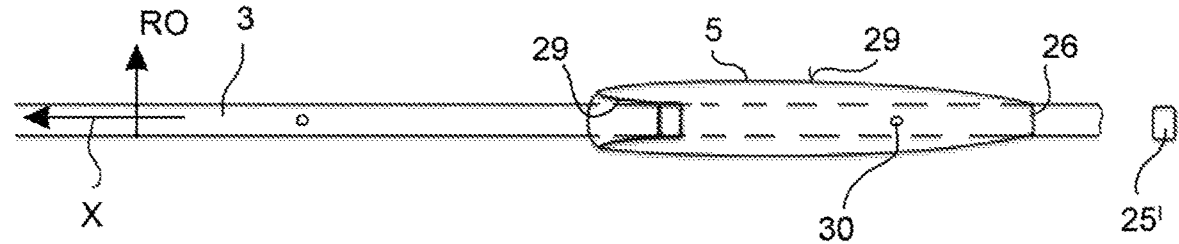
Figure 14:
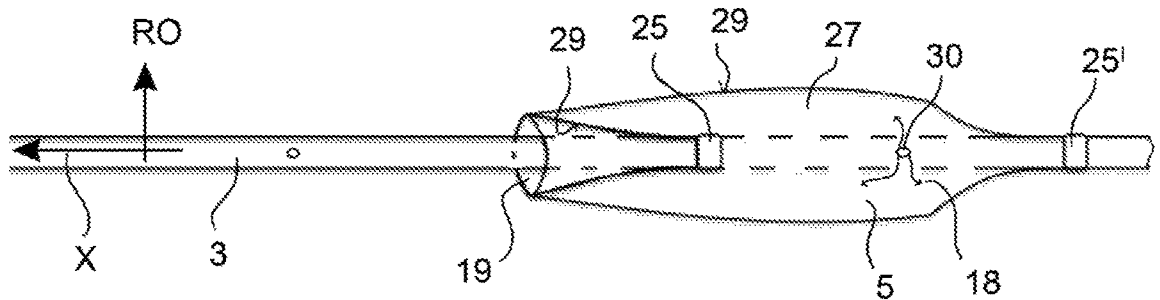
Figure 14:
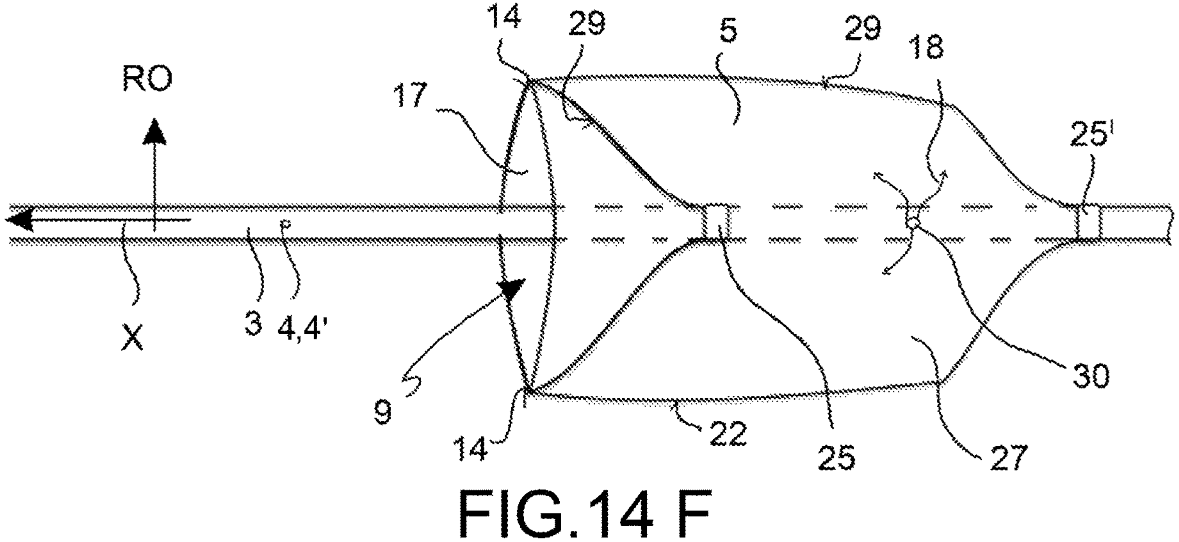
Figure 15:
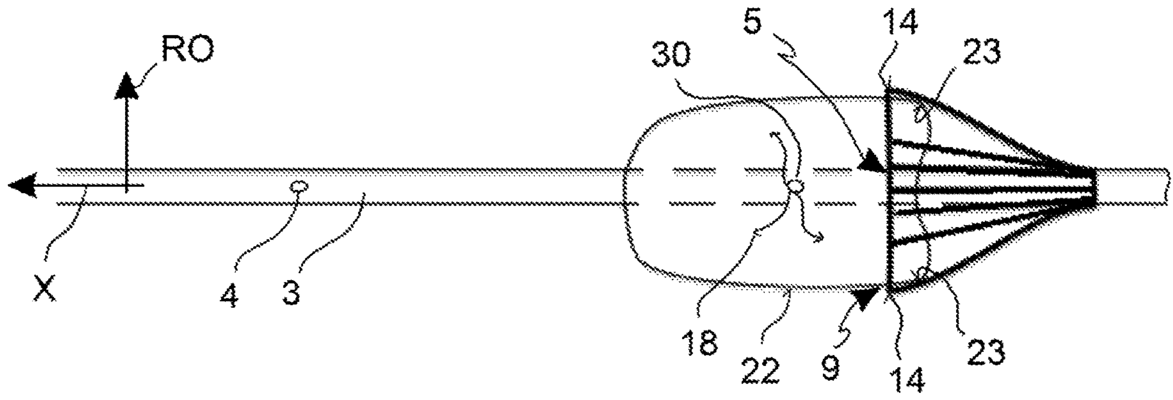
Figure 15:
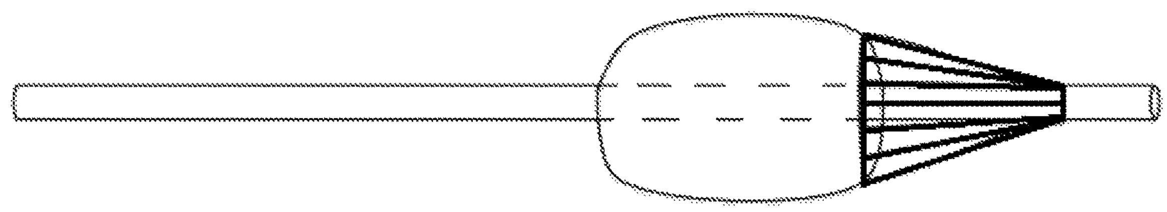
Figure 15:
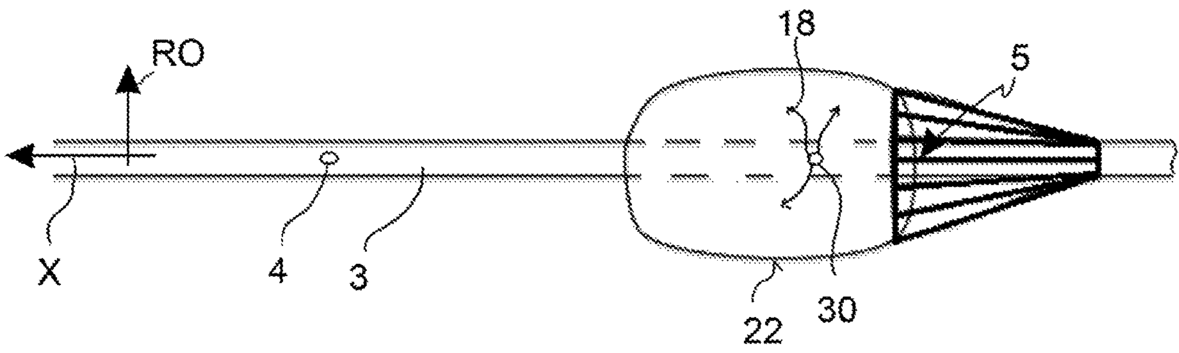
Figure 16:
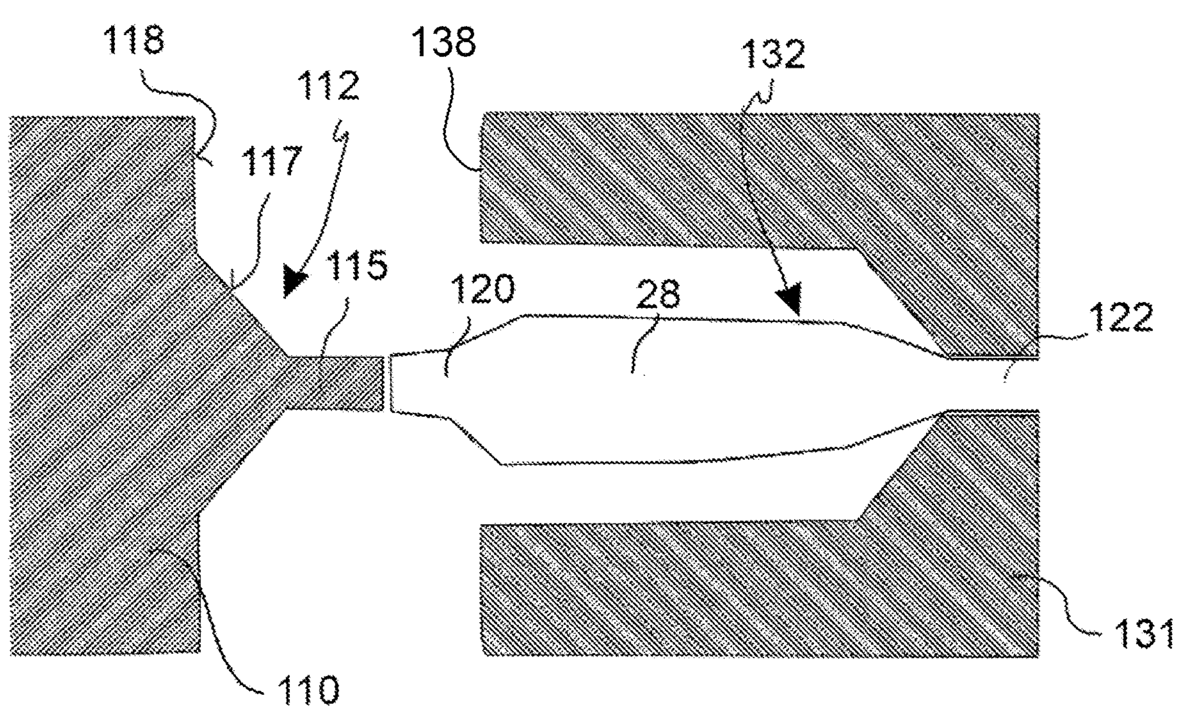
Figure 16:
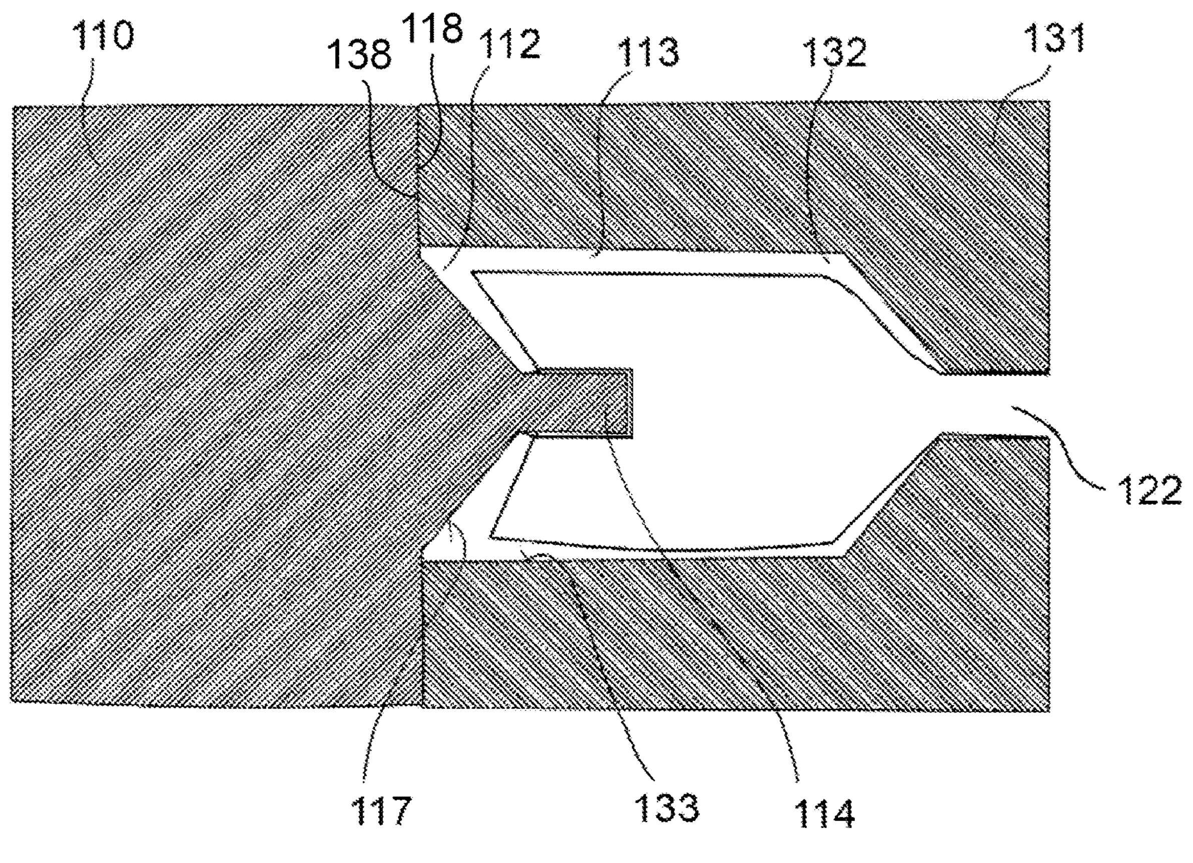
Figure 18A:
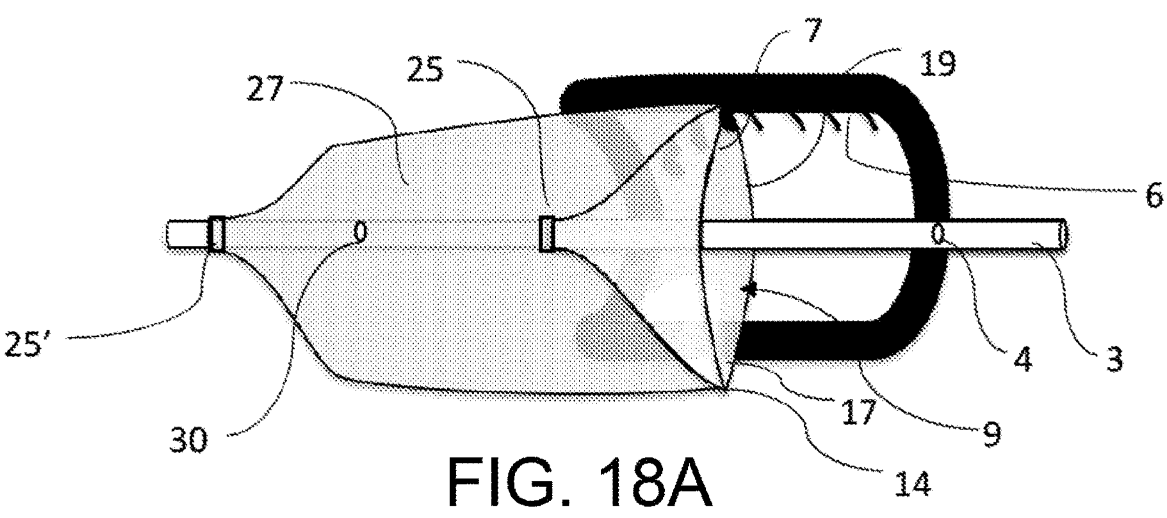
Figure 18B:
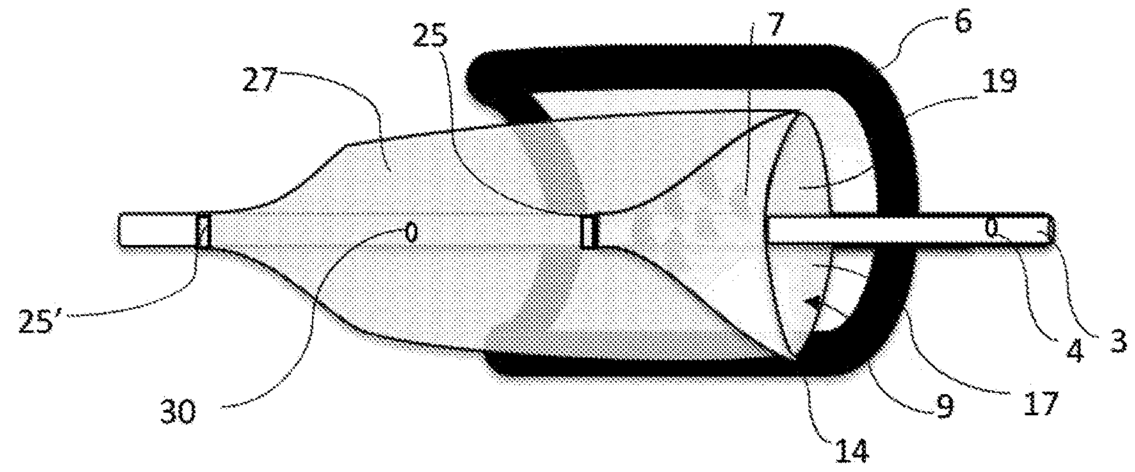
Figure 18C:
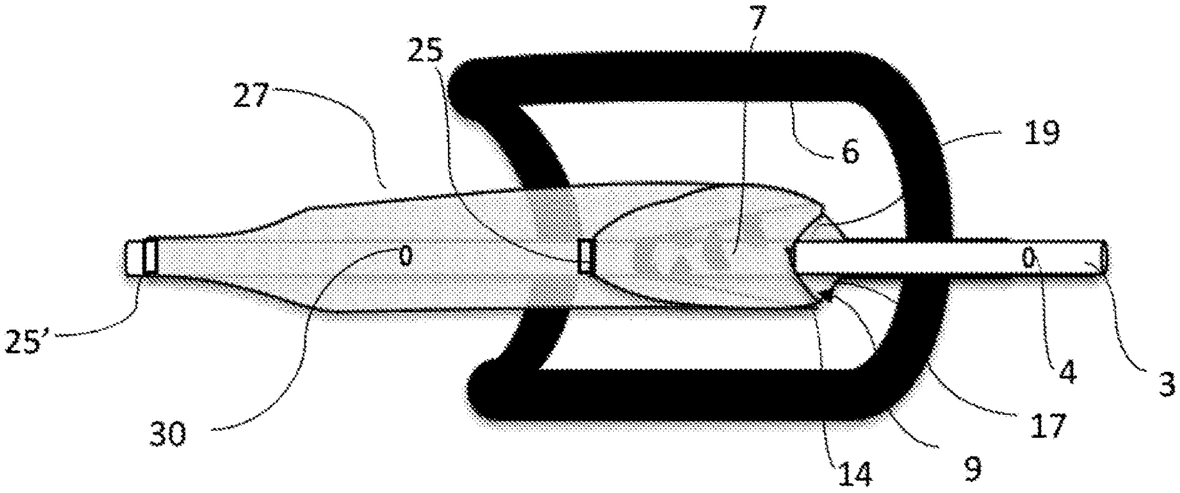

Further features and advantages of the invention will become apparent from the description provided below of preferred exemplary embodiments thereof, given by way of non-limiting example, with reference to the accompanying drawings, in which:

FIG. 1 diagrammatically shows a vascular device, according to an embodiment;

FIG. 2 A diagrammatically shows an abrasion element inside a blood vessel, according to an embodiment, in which the abrasion element is in the rest configuration;

FIG. 2 B shows the abrasion element of FIG. 2 A when in contact configuration;

FIGS. 3 A and 3 B diagrammatically sectionally show a portion of the abrasion element intended to come into contact with the inner wall of the blood vessel, according to some embodiments;

FIG. 4 diagrammatically shows a vascular device, according to an embodiment;

FIG. 5 diagrammatically shows a vascular device, according to an embodiment, during the dispensing of a pharmacological agent;

FIG. 6 diagrammatically shows an abrasion element of a vascular device, according to an embodiment;

FIG. 7 diagrammatically shows the inflation of an expandable abrasion element, according to an embodiment;

FIG. 8 A diagrammatically shows an abrasion element inside a blood vessel, according to an embodiment, in which the abrasion element is in the rest configuration;

FIG. 8 B diagrammatically shows an abrasion element inside a blood vessel, according to an embodiment, in which the abrasion element is in the rest configuration;

FIG. 9 is an axonometric view which diagrammatically shows an abrasion element, according to an embodiment;

FIG. 10 diagrammatically shows an abrasion element inside a blood vessel, according to an embodiment, FIG. 11 diagrammatically shows an abrasion element inside a blood vessel, according to an embodiment, FIG. 12 A diagrammatically shows an abrasion element inside a blood vessel, according to an embodiment, in which the abrasion element is in the rest configuration;

FIG. 12 B shows the abrasion element of FIG. 16 A when in contact configuration;

FIGS. 13 A, 13 B and 13 C show some steps of a treatment sequence, according to a possible operating mode;

FIGS. 14 A, 14 B, 14 C, 14 D, 14 E and 14 F show some steps of a sequence of a method for forming an abrasion element, according to an embodiment;

FIGS. 15 A, 15 B and 15 C show some steps of a sequence for bringing an abrasion element in contact configuration, according to an embodiment;

FIGS. 16 A and 16 B show some steps of a method for forming an abrasion element, according to an embodiment;

FIGS. 17 A to 17 D show some steps of a method for forming an abrasion element, according to an embodiment;

FIGS. 18A-18C diagrammatically show the device according to the present invention, in which the abrasion element is inside a partially dissected blood vessel, and is in contact configuration in FIG. 18A, in which the abrasion element being fed to remove material from the inner wall of the vessel section and collect the material in the collection portion is visible; in FIG. 18 B the abrasion element is in the rest configuration with the contact portion spaced from the inner wall and with the removed material in the collection portion; and in FIG. 18 C, the abrasion element is in the rest configuration with the contact portion near the intraluminal element so as to retain the collected material in the collection portion, preventing tissue and pharmacological agent residues from being circulated in the bloodstream.

DETAILED DESCRIPTION OF SOME EMBODIMENTS

In accordance with a general embodiment, a vascular device 1 is included for treating at least one blood vessel tract 2. Preferably, the vascular device 1 is a vascular catheter 1.

The vascular device 1 comprises at least one intraluminal element 3, for example a catheter shaft 3 of said vascular catheter 1, having at least one opening for dispensing drug 4 in the blood vessel tract 2. The intraluminal element 3 is intended to be inserted inside a blood vessel 2.

Preferably, the drug dispensing opening 4 opens from the intraluminal element 3 and is in fluid communication with a drug reservoir containing pharmacological agent D, for example a sclerosing agent D, in which the drug reservoir is mounted on the proximal portion of the vascular catheter 1 which preferably comprises a catheter handpiece 15. The intraluminal element 3, for example a shaft 3 of a vascular catheter 1, preferably comprises a distal end 24 adapted to be received in a blood vessel tract 2 and a proximal end adapted to remain outside the blood vessel 2.

The pharmacological agent D can be in liquid form or in the form of a sclerosing foam, for example containing air or nitrogen, and is preferably injected in a blood vessel tract 2 of a patient by means of the vascular catheter 1. For this purpose, the vascular catheter 1 can comprise a treatment assembly 10, adapted to perform a pharmacological treatment on the inner wall 6 of the blood vessel 2, the treatment assembly 10 comprising said dispensing opening 4. The at least one dispensing opening 4 can be arranged near the distal portion of the intraluminal element 3, for example the distal portion of a catheter shaft 3.

The vascular device 1 further comprises at least one abrasion element 5 intended to come into contact with the inner wall 6 of the blood vessel tract 2 to remove material 7 from said inner wall 6.

By virtue of the inclusion of the abrasion element 5, the vascular device 1 is capable of applying a pharmacological treatment and also applying a mechanical abrasion treatment to the inner wall 6 of the blood vessel 2.

According to a preferred operating mode, first the pharmacological treatment is performed, dispensing pharmacological agent D from said drug dispensing opening 4 on the inner wall 6 of the intraluminal element 3, and then the mechanical abrasion treatment is performed by means of said at least one abrasion element 5. Thereby, the mechanical treatment is aimed at removing biological material already treated pharmacologically and typically, when the endothelial layer of the inner wall of the vessel 2 is subjected to a sclerosing treatment, dead endothelial and muscle cells are formed, which are thus removed due to the mechanical abrasion treatment.

The abrasion element 5 is connected to the intraluminal element 3 and comprises a contact portion 14 adapted to remove the material 7 treated with the pharmacological agent D from the inner wall 6.

The abrasion element 5 comprises at least a first surface 17, 23 adapted to face the intraluminal element 3 and configured to face the fluid inside the blood vessel.

The abrasion element 5 is preferably adapted to perform a scraping operation of the inner wall 6 of the blood vessel 2 while it scrapes the inner wall 6, like a spatula or a plow.

The inclusion of the abrasion element 5 dragged against the inner wall 6 allows material 7 to be scraped and removed from the inner wall 6 after the drug has been dispensed on the inner wall 6 and after the dispensed drug has carried out the therapeutic action thereof towards said inner wall 6 of the blood vessel 2, for example a vein.

The at least one abrasion element 5 is preferably adapted to abrade the entire circumferential transverse section of the inner wall of the blood vessel 2. In other words, the at least one abrasion element 5 is preferably adapted to remove material from the entire circumferential transverse section of the inner wall of the blood vessel 2.

It should be noted that the wall material which is abraded by the abrasion element 5 consists of dead endothelial cells, basement membrane, dead smooth muscle cells, connective tissue, proteins, mupolysaccharides, proteoglycans, elastin, collagen fibers, endothelin, chemokines, selectins, integrins . . . etc. which form a sort of biological sludge with the density of mud consisting mainly of dead cells, a kind of aggregate of macromolecules and cells which can easily disperse disintegrated in the bloodstream and thus cannot be collected or extracted as if it were a single compact layer similar to the layer of skin which would be taken with a dermatome.

The abrasion element is configured to expand with respect to the intraluminal element 3 at least in a radial direction transverse to the main longitudinal extension direction of the vessel and/or of the intraluminal element 3 between at least one rest configuration and at least one contact configuration, in which, in the contact configuration, the contact portion 14 is in contact with the inner wall 6, and, in the rest configuration, the contact portion 14 is spaced from the inner wall 6.

In accordance with an embodiment, the abrasion element 5 is reversibly and selectively movable between the rest configuration and the contact configuration. In accordance with an embodiment, the rest configuration is a configuration for transporting the device inside a blood vessel until the portion of the vessel to be pharmacologically treated is reached. In accordance with an embodiment, the rest configuration is a configuration for transporting the removed material 7 from the portion of the pharmacologically treated vessel out of the blood vessel, avoiding dispersing pharmacological residues and pharmacologically treated material 7 into the blood stream.

The at least a first surface 17, 23 adapted to face the intraluminal element 3 forms, at least in said contact configuration, a concave portion 19 adapted to face the fluid inside the blood vessel, in which said collection portion 9 comprises said concave portion 19 so as to collect the material 7 removed from the inner wall 6 treated with the pharmacological agent D.

In accordance with an embodiment, the concave portion 19 has a concavity facing the at least one opening 4 for dispensing the pharmacological agent D, so as to make it possible to remove the material 7 from the inner wall 6 of the vessel tract after it has been pharmacologically treated, collecting the removed material 7 in the concave portion by moving the abrasion element 5 in the direction of the at least one opening 4 along an advance direction. In accordance with an embodiment, the abrasion element 5 comprises an element which is deformable in the outer radial direction RO adapted to selectively assume said at least one contact configuration in which it is in contact with the inner wall 6. The deformation of the deformable element can be an expansion.

In accordance with an embodiment, the abrasion element 5 comprises an element which is expandable in the outer radial direction RO adapted to selectively assume said at least one contact configuration in which it is in contact with the inner wall 6.

The expandable element of the abrasion element 5 can expand on command.

In accordance with a preferred embodiment, the expandable element of the abrasion element 5 is also adapted to assume said at least one rest configuration in which it is not in contact with the inner wall 6.

In accordance with an embodiment, between said contact configuration and said rest configuration, said contact portion 14 approaches said intraluminal element 3 closing said concave portion 19 in the direction of said intraluminal element 3 so as to retain the removed material 7.

In accordance with an embodiment, in said rest configuration, said contact portion 14 is directly or indirectly in contact with said intraluminal element 3 so as to retain the removed material 7 inside the collection portion 9 avoiding dispersing the removed material 7 in the bloodstream.

In accordance with an embodiment, said abrasion element 5 is reversibly expandable between said contact configuration and said rest configuration.

In accordance with an embodiment, the abrasion element 5 comprises an attachment portion connected to the intraluminal element 3. In accordance with an embodiment, the attachment portion is circumferentially connected to the intraluminal element 3.

In accordance with an embodiment, said first surface 17, 23 extends between said attachment portion and said contact portion 14 at least in the direction of said at least one opening 4 for dispensing the drug. In accordance with an embodiment, said concave portion 19 has a concavity facing the at least one opening 4 for dispensing the drug. In accordance with an embodiment, the collection portion 9 defines an annular collection area around the intraluminal element 3. In accordance with an embodiment, said collection portion 9 forms an annular collection chamber around the portion of intraluminal element 3 to which said first surface 17, 23 faces.

In accordance with an embodiment, the at least one opening 4, at the end of the treatment, acts as a suction opening 4' for the recovery of the drug previously dispensed in the chamber interposed between two plug elements 12. In accordance with an embodiment, the intraluminal element 3 comprises a suction opening 4' and a dispensing opening 4. In accordance with an embodiment, the at least one suction opening 4' is configured to suction the material 7 removed from the inner wall 6 and collected in the collection portion 9 of the abrasion element 5 which acts as one of the two plug elements 12. By virtue of the inclusion of the suction opening 4' it is possible to suction between the two plug elements 12, substances such as dead cellular material, substances produced and released by the endothelial cells of the vessel wall such as endothelin, a substance which has significant vasoconstrictive power and is responsible for symptoms such as cerebral or cardiac ischemia.

In accordance with an embodiment, the collection portion 9 extends at least partially around the at least one opening 4 or the at least one suction opening 4'.

In accordance with an embodiment, the collection portion 9 extends around the portion of intraluminal element 3 which has the at least one opening 4 or the at least one suction opening 4'.

The body of the expandable element of the abrasion element 5 can comprise said attachment portion, connected to the intraluminal element 3, the contact portion 14 with the inner wall 6 of the blood vessel 2, in which the body of the expandable element of the abrasion element 5 is designed to move the position of the contact portion 14 in a radial direction, in order to selectively perform an abrasion of material 7 from the inner wall 6. The contact portion 14 is preferably a surface having a substantially circumferential extension. For example, the contact portion 14 can be formed by a circumferential edge. In accordance with an embodiment, the contact portion 14 comprises a circumferential edge of said abrasion element 5.

In accordance with an embodiment, said expandable element comprises the contact portion 14 and the first surface 17, 23.

In accordance with a preferred embodiment, the abrasion element 5 comprises an inflatable balloon, for example a surgical balloon adapted to be inflated with inflation fluid 18, for example physiological solution 18.

The intraluminal element 3 preferably comprises at least one inflation opening 30 in fluid communication with the interior of the inflatable balloon for introducing or extracting inflation fluid 18 into or from the inflatable balloon. The handpiece 15 of the vascular device 1 can comprise a control interface having a control for inflating and/or deflating the inflatable balloon on command which forms the abrasion element 5.

The inflatable balloon of the abrasion element 5 can comprise on the outer surface 22 thereof a contact portion 14 adapted to perform the abrasive action on the inner wall 6 of the blood vessel 2.

In accordance with an embodiment, the inflatable balloon is adapted to cooperate with said expandable element so as to bring said contact portion 14 into contact with said inner wall 6 by inflating and/or deflating said inflatable balloon. In accordance with an embodiment, said inflatable balloon comprises an outer surface 22. In accordance with an embodiment, said collection portion 9 is defined between a balloon outer surface 22 and said radially outer portion 23.

In accordance with an embodiment, said first surface 17, 23 comprises a radially inner portion and a radially outer portion 23. In accordance with an embodiment, the balloon outer surface 22 is partially in contact with said radially inner portion. In accordance with an embodiment, said collection portion 9 is an annular portion radially extending between a circumferential edge of the contact portion 14 and a balloon outer surface 22, and longitudinally between the balloon outer surface 22 facing the radially outer portion 23, substantially forming an annular niche.

The abrasion element 5 can comprise, in addition to the inflatable balloon, a deformable element, the expanding inflatable balloon cooperates with the deformable element to bring a contact portion 14 into contact with the inner wall 6 of the blood vessel 2. For example as shown in FIG. 10, an expandable element is fitted on an inflatable balloon so that the outer wall 22 of the inflatable balloon is adapted to push an inner wall 23 of the expandable element in an outer radial direction RO so as to bring a contact portion 14 of the expandable element in contact with the inner wall 6 of the blood vessel 2.

In accordance with an embodiment, the abrasion element 5 comprises an expandable mechanism, for example comprising tie-rods 8. The inclusion of tie-rods 8 for example operatively connected to radially peripheral parts of the abrasion element 5 and to an element slidably fitted on the intraluminal element 3 allows forming a reinforced connection between the abrasion element 5 and the intraluminal element 3. For example, a slider 16 can be included slidably fitted on the intraluminal element 3, tie-rods 8 are placed between the slider 16 and the peripheral portions of the abrasion element 5 so that by acting on the slider 16 it is possible to tension such tie-rods 8 bringing for example the expandable abrasion element 5 into a rest configuration. In accordance with an embodiment, the abrasion element 5 comprises an intra-vascular umbrella structure expandable in the outer radial direction RO, as shown for example in FIG. 9, which can be fitted on the intraluminal element 3.

The expandable abrasion element 5 is further adapted to contract radially.

In accordance with an embodiment, the abrasion element 5 comprises a hinge 20 or the like near or at the intraluminal element 3, so that the body of the abrasion element 5 is hinged near or at the intraluminal element 3 and/or the attachment portion. By virtue of such a hinge 20, the expansion in the outer radial direction RO of the abrasion element 5 is allowed.

The abrasion element 5 can comprise one or more reinforcing elements 21 adapted to locally reinforce a portion of the abrasion element 5. For example, said reinforcing elements 21 can comprise radial reinforcements and/or circumferential reinforcements. In accordance with an embodiment, the abrasion element 5 comprises reinforcing elements 21 in order to exert an improved mechanical abrasion action of material from the inner wall 6 of the blood vessel 2, such as spurs 21, rostrums 21, and/or the like. The one or more reinforcing elements 21 can comprise a sharp edge.

In accordance with an embodiment, said one or more reinforcing elements 21 comprise at least one rib 21 surrounding the body of the abrasion element 5 projecting in the outer radial direction RO. The at least one rib 21 can be a helix which wraps around the body of the expandable element, for example an inflatable balloon. The at least one rib 21 can be a ring which embraces the body of the expandable element, for example an inflatable balloon.

As shown for example in FIGS. 12 A-B, the reinforcing element 21 can be made in the form of an annular spur.

As shown for example in FIG. 12 A, the intraluminal element 3 can comprise a tapered or flared portion 31 of reduced radial diameter to receive the abrasion element 5 when in the rest configuration, so as to minimize the radial bulk of the abrasion element 5 when in the rest configuration.

In accordance with an embodiment, the abrasion element 5 comprises an element adapted to radially expand inside the blood vessel 2, i.e., adapted to expand in the outer radial direction RO. For example, bellows processing can be included on a sleeve slidably fitted on the intraluminal element 3.

In accordance with an embodiment, the abrasion element 5 comprises an element adapted to radially expand inside the blood vessel by the sail effect. For example, the abrasion element 5 comprises a first surface 17 facing the fluid inside the blood vessel 2 which tends to swell like a sail when the vascular device 1 is fed into the blood vessel 2, bringing itself into an expanded contact configuration with the inner wall 6 of the vessel 2 in a substantially automatic manner as a response to the feeding movement of the abrasion element 5 inside the blood vessel 2.

The feeding of the abrasion element 5 inside the blood vessel 2 is preferably determined by the movement of the intraluminal element 3. For example, the abrasion element 5 is fixed integral with a portion of the intraluminal element 3, for example a shaft 3 of a vascular catheter 1. By moving the intraluminal element 3 in the longitudinal direction inside the blood vessel 2, the feeding of the abrasion element 5 is determined.

The term "feeding" is not necessarily meant to indicate distally directed movement. The feeding movement can be directed proximally or distally as needed.

Preferably, the abrasion element 5 is placed on a portion of the intraluminal element 3 which is more distal with respect to the dispensing opening 4 for dispensing the sclerosing drug, and the movement of the intraluminal element 3 which determines the feeding of the abrasion element 5 occurs in the proximal direction, for example by pulling the intraluminal element 3 proximally. This allows performing the mechanical abrasion action on the inner wall of the vein only after the wall has been previously treated with a temporal contact exposure of a drug D on the wall itself.

The abrasion element 5 does not necessarily reach the contact configuration by expanding the volume thereof, although according to a preferred embodiment it does, and for example the abrasion element 5 can reach the contact configuration by contracting the volume thereof. For example, to reach the contact configuration, the abrasion element 5 moves a contact portion 14 in the outer radial direction RO, i.e., in the direction from the intraluminal element 3 to the inner wall 6. During this movement in the outer radial direction RO, the body of the abrasion element 5 can expand radially in volume or it can move radially outward, for example leaving at least one through opening, for example a fine filter, near the intraluminal element 3 for the fluid inside the blood vessel 2.

For example, to reach the contact configuration, the abrasion element 5 faces said first surface 17 to the fluid present in the blood vessel 2, and such a first surface 17 can inflate by the sail effect. The sail effect is achieved by the relative movement between the abrasion element 5 and the blood vessel 2. For example, the relative movement between the abrasion element 5 and the blood vessel 2 is achieved by feeding the intraluminal element 3 inside the blood vessel 2 in a advance direction X. The advance direction X can be directed distally or proximally.

The at least one abrasion element 5 comprises said at least one contact portion 14, intended to perform the removal of material from the inner wall 6. Said contact portion 14 can have an increased section 21 with respect to the rest of the abrasion element 5 and the increased section forms a reinforcing element 21. For example, the abrasion element 5 is made in the form of a surgical balloon which is inflatable by means of inflation fluid 18 through the intraluminal element 3, for example a shaft 3 of a vascular catheter 1, and at the contact portion 14 intended to remove material 7 from the inner wall 6 of the blood vessel 2, the balloon has a greater thickness, forming a sort of reinforcement to perform the removal of the material 7. Said contact portion 14 preferably has a surface processing aimed at increasing the roughness thereof. For example, the contact portion 14 can be corrugated or pleated, to favor the abrasive power on the inner wall 6. For example, the contact portion 14 can comprise surface knurling processing.

The abrasion element 5 forms a concave portion 19 adapted to face the fluid inside the blood vessel 2. The concave portion 19 is formed by said first surface 17. The fluid inside the blood vessel 2 which faces the concave portion 19 does not necessarily comprise blood since it can be an isolated section 11 of blood vessel 2 temporarily isolated from the circulation of blood.

The abrasion element 5 can be made in the form of an expandable surgical balloon overturned on the intraluminal element 3 of the vascular device 1, and the concave portion 19 can be formed by the shape assumed by the surgical balloon after having fastened it to the intraluminal element 3 and overturned.

In accordance with a possible operating mode, a manufacturing method of an expandable balloon 5 having at least one concave portion 19 comprises the steps of:

- providing a mold cavity 113 having at least one concave portion 112 delimited by a first wall having a protrusion 114 which projects in the mold cavity 113;
- providing a preform 120 or parison 120 for expandable balloons 5, for example which delimits a cavity 28, blind or through;
- fitting the parison 120 on the protrusion 114 of the die 110 of the mold.

Preferably, a mold can be included for forming an expandable balloon 5 suitable for medical-surgical applications having a die 110 comprising a first wall which at least partially delimits a concave portion 112 of a mold cavity

113; said first wall comprising a protrusion 114 adapted to project cantilevered in said mold cavity 113 forming a free protrusion end 115 and a protrusion root opposite said free end 115, and a mold tapered surface 117 which tapers as it approaches said protrusion root. Preferably, said protrusion 114 has a substantially cylindrical shape. Preferably, said protrusion root is joined to the tapered surface 117. Preferably, the protrusion 114 and the tapered surface 117 are made in a single piece. The tapered surface 117 is preferably substantially frustoconical. The mold can further comprise at least one counter-die 131 which at least partially delimits a convex portion 132 of said mold cavity 113. The counter-die 131 can comprise side walls 133 which delimit the cavity 113. Preferably, the die 110 comprises an abutment portion 118 and the counter-die 131 comprises a counter-abutment portion 138, said abutment portion 118 and said counter-abutment portion 138 are adapted to mutually abut to delimit the mold cavity 113.

The manufacturing method can comprise at least one but also all of the following further steps of:

- overturning the parison 120 on the protrusion 114 of the die 110; and/or
- inserting the parison 120 in the mold cavity 113; and/or
- expanding the parison 120 in the concave portion 112 of the mold cavity 113.

As shown for example in the sequence shown in FIGS. 14 A-F, the abrasion element 5 is a surgical balloon, or an expandable balloon, made as a through deformable body, or parison 120, which delimits a through longitudinal cavity 28 with a surface 29 thereof facing the intraluminal element 3 which is fitted on the intraluminal element of the device 3, for example fitted by the distal end 24 of the intraluminal element 3, and sealingly fastened to the intraluminal element 3 by means of a fastening element 25 so that a free margin 26 is formed, i.e., not fastened to the intraluminal element 3 opposite the fastening element 25 with respect to the deformable body of the expandable balloon; subsequently, the free edge 26 is overturned and fastened with a fastening element 25' to the intraluminal element 3 in a position for example placed distally on the intraluminal element 3 with respect to where the fastening element 25 is placed; thereby, an inner chamber 27 is formed which can be inflated by inflation fluid 18; thereby, the surface 29 of the balloon portion which has been overturned will face the outside of the chamber 27 and therefore opposite with respect to the intraluminal element 3, due to the effect of the overturning; by inflating the inner chamber 27 it is possible to expand the expandable balloon; the local stiffness and/or the shape of the expandable balloon can be chosen so that a collection portion 9, for example a collection niche, is formed as a result of the overturning and subsequent fastening. The collection portion 9 can have a concave shape, for example substantially conical and/or a substantially annular conformation.

In accordance with an embodiment, said parison 120 and/or said surgical balloon 5 is an elastomer or an extensible polymer.

In accordance with an embodiment, said extensible polymer is a thermoplastic elastomer.

In accordance with an embodiment, said extensible polymer comprises individually or in a mixture at least one of polyethylene, polyethylene terephthalate, polytetrafluoroethylene, polyamides, polyvinyl chloride, latex, silicones, polyurethane copolymers, polyamide copolymers, copolymers of polyamide and polyethers.

In accordance with an embodiment, said surgical balloon 5 is made of a compliant and/or semi-compliant material.

In accordance with an embodiment, said parison 120 has a multilayer parison body, comprising a first elastomeric layer and a second thermoplastic layer. In accordance with an embodiment, said parison 120 comprises a non-compliant layer. In accordance with an embodiment, said parison 120 is made of a material adapted to make a compliant or semi-compliant expandable balloon.

In accordance with a preferred embodiment, the surgical balloon is fitted on the intraluminal element 3, and the intraluminal element 3 comprises at least one inflation opening 30 in fluid communication with the interior of the surgical balloon for introducing into or extracting from the surgical balloon the inflation fluid 18 so as to reversibly expand or contract the abrasion element 5 between the rest configuration and the contact configuration.

In accordance with an embodiment, the abrasion element 5 has a balloon longitudinal extension axis around which the balloon extends. In accordance with an embodiment, the abrasion element 5 extends with cylindrical symmetry around said balloon longitudinal extension axis. In accordance with an embodiment, said radial direction RO is transverse with respect to said balloon longitudinal extension axis.

In accordance with an embodiment, the surgical balloon is sealingly fastened on the intraluminal element 3 with a first fastening element 25 and a second fastening element 25' so as to define a fluid-tight chamber in fluid connection with the inflation opening 30 between an inner surface of the surgical balloon and a surface of the intraluminal element 3 between the first fastening element 25 and the second fastening element 25', in which the concave portion 19 extends from the first fastening element 25 to said contact portion 14. In accordance with an embodiment, the concave portion 19, at least in the contact configuration, has an at least partially conical shape. In accordance with an embodiment, the collection portion 9 is joined to the contact portion 14 so that the material 7 removed from the contact portion 14 is directed in the collection portion avoiding interfering with the contact portion 14. In accordance with an embodiment, at least in the contact configuration, the collection portion 9 forms a funnel-shaped portion configured to facilitate the collection of the removed material 7 by feeding the device 1 inside the blood vessel along the advance direction X. In accordance with an embodiment, the collection portion 9 and the contact portion 14 are integrated in the same element.

In accordance with an embodiment, the abrasion element 5 has a first attachment portion and a second attachment portion configured to be connected to the intraluminal element 3 by means of the first fastening element 25 and the second fastening element 25', in which the first attachment portion and the second attachment portion are circumferential, preferably cylindrical portions adapted to receive the intraluminal element 3, in which the first attachment portion and the second attachment portion are spaced by an attachment distance D along a longitudinal extension direction of the intraluminal element 3 or along the longitudinal extension axis of the balloon around which the abrasion element 5 extends. In accordance with an embodiment, the attachment distance D is between 20 mm and 150 mm.

In accordance with an embodiment, when said balloon is in said expanded configuration, a projection of the concave portion 19 and/or of said first wall 17 on the longitudinal extension axis of the balloon defines a segment having a concave portion length C. In accordance with an embodiment said concave portion length C is between 2 mm and 30 mm, preferably between 5 mm and 15 mm. In accordance with an embodiment, said concave portion length C is the height of the truncated cone delimiting the concave portion 19. In accordance with an embodiment, said concave portion length is the height of the truncated cone delimiting the concave portion 19. In accordance with an embodiment, said concave portion length C is between ⅙ and ½ of the attachment distance D.

By virtue of the inclusion of the collection portion 9, it is possible to scrape and transport the removed material 7 from the inner wall 6 of the blood vessel 2 out of the blood vessel 2.

In accordance with an operating mode shown for example in FIGS. 16-A and 16-B, the parison 120 or preform 120 approaches a protrusion 114 of the die 110 with a closed margin thereof, i.e., unadapted to allow access to the cavity 28 and the parison 120 is shaped to the protrusion 114. The counter-die 131 is thus abutted against the die 110. The parison 120 is subsequently expanded by inflating through the channel 122. The shape of the concave portion 112 of the mold cavity 113 allows making an expandable balloon 5 having a concave portion 19.

In accordance with a preferred embodiment, the abrasion element 5 forms a collection portion 9 for collecting the removed material 7 from the inner wall 6.

The joint inclusion on a single device, such as a vascular catheter 1, of the abrasion element 5 and of the collection portion 9 allows making a system which at the same time scrapes or scratches the inner wall 6 removing material and scraping the removed material 7, avoiding freeing cellular and pharmacological debris in the bloodstream using a single vascular device 1 having an intraluminal element 3.

The collection portion 9 can be formed by the concave portion 19.

By virtue of the collection of the removed material 7 in the collection portion 9, for example a collection niche, debris or other material removed from the inner wall 6 of the blood vessel 2 is prevented from entering the blood vessel 2, greatly reducing the risk of complications such as inflammations localized or distributed along the vascular path, or in the lung which is the organ of collection of all the venous blood coming from the periphery.

As shown for example in the sequence shown in FIGS. 15 A-C, an inflatable balloon cooperates with an expandable element, shown here as an expandable frustoconical body, so that by inflating the inflatable balloon, the balloon outer surface 22 is pushed against a surface 23 facing the intraluminal element 3 of the expandable frustoconical body, bringing a contact portion 14 of the expandable frustoconical body into contact with the inner wall 6 of the blood vessel 2. A collection portion 9, for example of an annular mouth, can be formed between the contact portion 14 and the balloon outer surface 22.

The at least one opening for dispensing drug 4 in the blood vessel tract 2 can be made as part of a treatment assembly 10 adapted to isolate a blood vessel volume 11 in contact with the inner wall 6 of the blood vessel 2. By isolating a blood vessel volume 11 or chamber 11 from the circulation of blood, it is possible to both control the concentration of the pharmacological agent D in such a volume 11, and to control the contact time of the pharmacological agent D against the inner wall 6 of the blood vessel 2.

In accordance with a preferred embodiment, said treatment assembly 10 further comprises one or more plug elements 12 adapted to isolate a blood vessel tract, and at least one core element 13, in which said at least one core element 13 determines a blood vessel volume 11 intended to come into contact with the inner wall 6. For example, the plug elements 12 and the core element 13 are all expandable elements, such as inflatable surgical balloons. The inclusion of the core element 13 which occupies the neighboring area of the intraluminal element 3 allows the pharmacological agent D to be brought into contact with the inner wall 6 of the blood vessel 2, reducing the quantity of drug necessary for the treatment. The inclusion of said plug elements 12 allows the volume 11 or chamber 11 to be isolated from the circulation of blood. The plug elements 12 preferably delimit said volume 11 therebetween. The core element 13 can be made in a single piece with a plug element 12, for example they can both be formed by a single inflatable balloon.

Preferably, the core element 13 comprises a radially expandable inflatable balloon which is fitted on the intraluminal element 3 of the device 1, forming a substantially annular chamber 11, or volume 11, in contact with the inner wall 6. Such an inflatable balloon which forms the core element 13 is adapted to expand during inflation in the outer radial direction RO. In accordance with an embodiment, the core element 13 can be inflated so as to over-stretch the inner wall of the vessel, breaking the intercellular bonds.

In accordance with a preferred embodiment, at least one of said plug elements 12 also acts as an abrasion element 5 of the wall 6. Thereby, a single expandable element, for example an inflatable balloon, acts both as a plug element for isolating a volume 11 or a chamber 11 of the treatment assembly 10 from the circulation of blood and as an element for removing material from the inner wall of the vessel.

Preferably, first the expandable element acts as a plug element 12 to isolate a blood vessel tract 2 into which the pharmacological agent D is to be injected and then acts as an abrasion element 5 to remove material 7 from the inner wall 6 of that same blood vessel tract 2 just treated with the pharmacological agent D.

The intraluminal element 3 can be designed to translate inside the blood vessel 2, along the longitudinal extension axis of the vessel 2. The translation can occur both proximally and distally. Preferably, when in operating conditions, the translation occurs in the proximal direction. This translation in the proximal direction inside the blood vessel 2 can be achieved by substantially pulling the intraluminal element 3, for example a shaft 3 of a vascular catheter 1, in the proximal direction.

In accordance with an embodiment, the at least one abrasion element 5 is placed along the intraluminal element 3 of the device 1 behind the at least one drug dispensing opening 4 in a determinable advance direction X of the device 1 in the blood vessel 2. Thereby, when the intraluminal element 3 is fed, the same stretch of blood vessel 2 is exposed first to the chamber 11 of the treatment assembly 10 and then to the abrasion element 5. The advance direction X is substantially parallel or coincident with the longitudinal extension axis of the vessel to be treated.

Preferably, said at least one abrasion element 5 is placed distally with respect to said at least one opening for dispensing drug 4.

Alternatively, said at least one abrasion element 5 can be placed proximally with respect to said at least one opening for dispensing drug 4.

A method for treating a blood vessel will be described below. The method is preferably adapted to the sclerosing treatment of varices.

A method for treating a blood vessel 2 comprises the steps of:

dispensing pharmacological agent D on the inner wall 6 of a blood vessel tract 2;

removing material from the inner wall 6 of said blood vessel tract 2.

In accordance with a preferred operating mode, the material removal step is performed after the dispensing step.

According to a preferred operating mode, the method further comprises the step of collecting the removed material 7.

The step of collecting the removed material 7 avoids the risk of flooding the circulatory stream with debris, for example catabolites or metabolites, as well as residues of the active pharmacological agent D which could have undesirable side effects.

In accordance with an operating mode, the material removal step includes mechanical material removal. Preferably, the material removal step is performed by abrading the inner wall 6.

In accordance with an operating mode, the method is performed by a vascular device 1 according to any one of the embodiments described above.

In accordance with an operating mode, the method comprises the step of isolating a blood vessel tract from the circulation of blood. Preferably this isolating step is included prior to the drug dispensing step.

In accordance with an operating mode, the removal step is performed by a deformable element expandable in the outer radial direction RO.

In accordance with an operating mode, both the removal and the collection steps are performed by the same deformable element expandable in the outer radial direction RO which is provided with a contact portion 14 and a collection portion 9.

In accordance with an operating mode, the method comprises the step of making two convex balloons, and associating them with each other in a respective edge 126, 126' to form a single balloon having a concave portion 109, avoiding including a mold having a concave portion 112. Preferably, the method comprises the step of providing two parisons 120, 120', each parison 120 and 120' being arranged in a respective pre-mold 123 and 123', and the step of expanding by inflating each parison 120 and 120' in the respective pre-mold 123 and 123', making two convex expandable balloons. Preferably, such pre-molds 123 and 123' are both convex, i.e., they are intended to form a convex balloon.

The association between the edges 126 and 126' of the convex balloons to form a balloon having a concave portion 109 preferably occurs by laser welding.

In accordance with an embodiment, such an association is performed by gluing. In accordance with an embodiment, such an association determines the formation of a concave portion 109 formed by one of the expandable balloons associated with each other in the respective edge 126, 126'.

Therefore, in accordance with a general embodiment, as shown for example in FIGS. 17-A to 17-D, a manufacturing method of an expandable balloon 105 for medical-surgical applications having at least one concave portion 109 comprises the steps of:

making two substantially convex preforms;

associating respective edges 126 and 126' of the convex preforms to each other, forming an expandable balloon 105 having a concave portion 109. Preferably, the concave portion 109 of the expandable balloon 105 is formed by one of the two convex preforms associated with each other. The preforms can for example be made as sheets of elastic material for expandable balloons.

The preforms can in turn be expandable balloons.

By virtue of the features described above provided separately or jointly with each other in particular embodiments, it is possible to obtain a device as well as a method which at the same time satisfy the above described requirements, contrasting each other, and the aforementioned desired advantages, and in particular:

it is possible to remove material from the wall of a vessel tract which has just been treated pharmacologically, for example just treated with a sclerosing agent;

between the pharmacological treatment and the material removal, the blood vessel wall is not exposed to physiological blood circulation, but is substantially isolated from the circulation;

it allows obtaining an abrasion element which is selectively activatable to remove material from the vessel wall;

an expandable element is created which has the dual function of isolating a chamber in contact with the vessel wall and removing material from the vessel wall;

the material removal is performed in a second moment after the pharmacological treatment, allowing material to be removed in an area of the wall already treated with a drug, for example a sclerosing drug;

it prevents the removed material as well as residues of pharmacological agent from dispersing into the bloodstream.

In order to meet contingent and specific needs, those skilled in the art may make several changes and adaptations to the above-described embodiments, and may replace elements with others which are functionally equivalent, without however departing from the scope of the following claims.

LIST OF REFERENCE NUMERALS

| | |
|---|---|
| 1 | Treatment device, e.g., vascular catheter |
| 2 | Blood vessel |
| 3 | Intraluminal element of the device, e.g., catheter shaft |
| 4, 4' | Drug dispensing opening and/or suction opening |
| 5 | Abrasion element |
| 6 | Inner vessel wall |
| 7 | Removed material |
| 8 | Tie-rod |
| 9 | Collection portion |
| 10 | Treatment assembly |
| 11 | Volume, or isolated volume, or chamber |
| 12 | Plug element |
| 13 | Core element |
| 14 | Contact surface, or contact wall of the abrasion element |
| 15 | Control handpiece |
| 16 | Slider |
| 17 | First surface |
| 18 | Inflation fluid |
| 19 | Concave portion |
| 20 | Hinge |
| 21 | Reinforcement |
| 22 | Balloon outer surface |
| 23 | Surface facing the intraluminal element of the expandable body or radially outer portion |
| 24 | Distal end of the intraluminal element |
| 25, 25' | Fastening element |
| 26 | Free margin |
| 27 | Chamber |
| 28 | Through longitudinal cavity |
| 29 | Surface |
| 30 | Inflation opening |
| 31 | Tapered section |
| 110 | Mold die |
| 112 | Concave portion of the mold cavity |
| 113 | Mold cavity |

-continued

| LIST OF REFERENCE NUMERALS | |
|---|---|
| 114 | Protrusion |
| 115 | Free end |
| 117 | Die tapered surface |
| 118 | Die abutment portion |
| 120 | Parison, or preform |
| 123, 123' | Pre-mold |
| 126, 126' | Edge |
| 122 | Blowing channel |
| 131 | Mold counter-die |
| 132 | Convex portion of the mold cavity |
| 133 | Counter-die side wall |
| 137 | Counter-die tapered surface, or second tapered surface |
| 138 | Counter-die counter-abutment portion |
| D | Pharmacological agent |
| X | Advance direction |
| RO | Outer radial direction |

The invention claimed is:

1. A vascular device for treating at least one tract of a blood vessel, comprising:

an intraluminal element comprising at least one dispensing opening for dispensing a pharmacological agent in the at least one tract of the blood vessel; and at least one abrasion element connected to the intraluminal element and adapted to come into contact with an inner wall of the blood vessel to remove material treated with the pharmacological agent from said inner wall, wherein said abrasion element comprises a contact portion adapted to obtain removal of the material from said inner wall, and wherein said abrasion element comprises a collection portion for collecting the material removed from said inner wall, wherein said abrasion element is configured to expand with respect to said intraluminal element at least in a radial direction transverse to a longitudinal extension direction of the blood vessel between at least one rest configuration and at least one contact configuration, wherein, in said at least one contact configuration, said contact portion is in contact with the inner wall, and, in said at least one rest configuration, the contact portion is spaced from the inner wall, wherein said abrasion element comprises at least a first surface facing said intraluminal element and configured to face a fluid inside the blood vessel, wherein said first surface, in said at least one contact configuration, forms a concave portion adapted to face the fluid inside the blood vessel, and wherein said collection portion comprises said concave portion so as to collect the material removed from the inner wall treated with the pharmacological agent, wherein said collection portion forms an annular collection chamber around a portion of the intraluminal element to which said first surface faces, wherein between said at least one contact configuration and said at least one rest configuration, said contact portion approaches said intraluminal element closing said concave portion towards said intraluminal element so as to retain the removed material, and wherein said concave portion has a concavity facing the at least one dispensing opening.

2. The vascular device of claim 1, wherein the abrasion element is an expandable surgical balloon, wherein the expandable surgical balloon has a first attachment portion fastened to the intraluminal element and an overturned portion that is overturned on the intraluminal element to form the concave portion; and/or wherein the overturned portion has a second attachment portion fastened to said intraluminal element, wherein said first attachment portion and said second attachment portion are circumferential portions adapted to receive the intraluminal element, and wherein said first attachment portion and said second attachment portion are spaced by an attachment distance along a longitudinal extension direction of the intraluminal element.

3. The vascular device of claim 1, wherein in said at least one rest configuration, said contact portion is directly or indirectly in contact with said intraluminal element to retain the removed material inside the collection portion avoiding dispersing the removed material in blood stream.

4. The vascular device of claim 1, wherein said abrasion element is reversibly expandable along said radial direction between said at least one contact configuration and said at least one rest configuration.

5. The vascular device of claim 1, wherein said abrasion element comprises an attachment portion circumferentially connected to the intraluminal element, and wherein said first surface extends between said attachment portion and said contact portion at least towards said at least one dispensing opening.

6. The vascular device of claim 1, wherein the contact portion is a surface having a substantially circumferential extension.

7. The vascular device of claim 1, wherein the contact portion comprises a circumferential edge of said abrasion element.

8. The vascular device of claim 1, wherein the abrasion element comprises an expandable mechanism comprising tie-rods.

9. The vascular device of claim 1, wherein the abrasion element comprises an element adapted to radially expand inside the blood vessel by sail effect, forming said concave portion.

10. The vascular device of claim 1, wherein said abrasion element is a surgical balloon fitted on the intraluminal element, and wherein the intraluminal element comprises at least one inflation opening in fluid communication with an interior of the surgical balloon to introduce in or extract from the surgical balloon an inflation fluid so as to reversibly expand or contract the abrasion element between the at least one rest configuration and the at least one contact configuration.

11. The vascular device of claim 10, wherein said surgical balloon is sealingly fastened on said intraluminal element with a first fastening element and a second fastening element so as to define a fluid-tight inner chamber in fluid connection with said at least one inflation opening between an inner surface of the surgical balloon and a surface of the intraluminal element between the first fastening element and the second fastening element, wherein said concave portion extends from said first fastening element to said contact portion, and wherein said concave portion, in said at least one contact configuration has an at least partially conical shape.

12. The vascular device of claim 1, wherein the abrasion element comprises an expandable element comprising said contact portion and said first surface, wherein said abrasion element comprises an inflatable balloon adapted to cooperate with said expandable element to bring said contact portion into contact with said inner wall by inflating and/or deflating said inflatable balloon, wherein said inflatable balloon comprises an outer surface, and wherein said collection portion is defined between a balloon outer surface and a radially outer portion.

13. The vascular device of claim 12, wherein said first surface comprises a radially inner portion and a radially outer portion, wherein the balloon outer surface is partially in contact with said radially inner portion, and wherein said collection portion is an annular portion extending radially between a circumferential edge of the contact portion and the balloon outer surface, and longitudinally between the balloon outer surface facing the radially outer portion and the radially outer portion, forming an annular niche.

14. The vascular device of claim 1, further comprising a treatment assembly adapted to isolate a volume of blood vessel in contact with the inner wall of the blood vessel comprising one or more plug elements adapted to isolate the at least one tract of the blood vessel, and at least one core element, said at least one core element determining the volume of blood vessel coming into contact with the inner wall, and wherein said at least one dispensing opening for dispensing the pharmacological agent in the at least one tract of the blood vessel is part of the treatment assembly.

15. The vascular device of claim 14, wherein the at least one core element comprises a radially expandable inflatable balloon fitted on the intraluminal element, forming a substantially annular chamber, or volume, in contact with the inner wall.

16. The vascular device of claim 14, wherein at least one of said plug elements is said abrasion element.

17. The vascular device of claim 14, wherein said intraluminal element comprises at least one suction opening configured to suction cellular debris or substances freed by cells of the material treated with the pharmacological agent contained between two plug elements at the end of a pharmacological treatment, or wherein said at least one dispensing opening is also a suction opening configured to suction the cellular debris or substances freed by the cells of the material treated with the pharmacological agent contained between two plug elements.

18. The vascular device of claim 1, wherein said collection portion is connected to said contact portion so that the material removed from the contact portion is directed in the collection portion, and/or wherein, in at least said contact configuration, said collection portion forms a funnel-shaped portion configured to facilitate collection of the removed material by feeding said vascular device inside the blood vessel.

19. The vascular device of claim 1, wherein said collection portion and said contact portion are integrated in the same element.

20. The vascular device of claim 1, wherein said contact portion comprises an increased section with respect to the rest of the abrasion element and the increased section forms a reinforcing element, and/or wherein the abrasion element comprises at least one reinforcing element for exerting an improved mechanical abrasion action of the material from the inner wall of the blood vessel, optionally the at least one reinforcing element being spurs or rostrums, and wherein the at least one reinforcing element comprises a sharp edge.

* * * * *